United States Patent
Tajima

(10) Patent No.: US 9,931,092 B2
(45) Date of Patent: Apr. 3, 2018

(54) RADIATION IMAGING SYSTEM AND OPERATION METHOD THEREOF, AND RADIATION IMAGE DETECTING DEVICE AND STORAGE MEDIUM STORING OPERATION PROGRAM THEREFOR

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 531 days.

(21) Appl. No.: 14/637,080

(22) Filed: Mar. 3, 2015

(65) Prior Publication Data
US 2015/0189194 A1  Jul. 2, 2015

Related U.S. Application Data

(63) Continuation of application No. PCT/JP2013/073286, filed on Aug. 30, 2013.

(30) Foreign Application Priority Data

Sep. 4, 2012  (JP) ................................. 2012-194582

(51) Int. Cl.
*A61B 6/00* (2006.01)
*G01T 1/02* (2006.01)
*H04N 5/32* (2006.01)

(52) U.S. Cl.
CPC .............. *A61B 6/488* (2013.01); *G01T 1/026* (2013.01); *A61B 6/4233* (2013.01);
(Continued)

(58) Field of Classification Search
CPC .... A61B 6/00; A61B 6/42; A61B 6/46; A61B 6/461; A61B 6/48; A61B 6/488;
(Continued)

(56) References Cited

U.S. PATENT DOCUMENTS

2012/0132820 A1* 5/2012 Iwakiri ................. G01T 1/2018
250/370.08
2013/0148782 A1* 6/2013 Tajima ................... A61B 6/542
378/62

FOREIGN PATENT DOCUMENTS

JP  2012-129984 A  7/2012
JP  2012-135588 A  7/2012

OTHER PUBLICATIONS

International Search Report, issued in PCT/JP2013/073286, dated Oct. 8, 2013.
(Continued)

*Primary Examiner* — Anastasia Midkiff
(74) *Attorney, Agent, or Firm* — Birch, Stewart, Kolasch & Birch, LLP

(57) ABSTRACT

In an X-ray imaging system, first X-ray irradiation and second X-ray irradiation are performed in performing X-ray imaging once. A preview producing circuit subjects first image data outputted from a sensor panel after the first X-ray irradiation is finished to binning processing or thinning processing to produce a preview image. The produced image is transmitted through a communication I/F to a console while the sensor panel performs an accumulation operation in the second X-ray irradiation. The preview image is displayed on a monitor of the console in the second X-ray irradiation.

20 Claims, 17 Drawing Sheets

(52) U.S. Cl.
CPC ............... *A61B 6/4283* (2013.01); *A61B 6/52* (2013.01); *A61B 6/5264* (2013.01); *A61B 6/542* (2013.01); *A61B 6/585* (2013.01); *H04N 5/32* (2013.01)

(58) Field of Classification Search
CPC ....... A61B 6/52; A61B 6/5205; A61B 6/5211; A61B 6/5229; A61B 6/5235; A61B 6/54; A61B 6/542; A61B 2562/00; A61B 2562/06; A61B 2562/066; G01T 1/00; G01T 1/02; G01T 1/026; G01T 1/16; G01T 1/163; G01T 1/24; G01T 1/246; G01T 7/00; G01T 7/12; G01T 7/005; G06T 2207/00; G06T 2207/10; G06T 2207/10064; G06T 2207/10116; G06T 2207/10121; G06T 2207/20212; G06T 2207/30; G06T 2207/30004; G01N 2223/00; G01N 2223/30; G01N 2223/304; G01N 2223/306; G01N 2223/40; G01N 2223/401; G01N 2223/406; G01N 2223/413; H04N 5/30; H04N 5/32; H04N 5/335; H04N 5/3355; H04N 5/347; H04N 5/351
See application file for complete search history.

(56) References Cited

OTHER PUBLICATIONS

Written Opinion of the International Searching Authority, issued in PCT/JP2013/073286, dated Oct. 8, 2013.

* cited by examiner

FIG.6

| BODY PART TO BE IMAGED | TUBE VOLTAGE (kV) | TUBE CURRENT (mA) | IRRADIATION TIME (msec) |
|---|---|---|---|
| ⋮ | ⋮ | ⋮ | ⋮ |
| CHEST AP | V1 | I1 | t1 |
| CHEST PA | V2 | I2 | t2 |
| ⋮ | ⋮ | ⋮ | ⋮ |

FIG.10

| BODY PART TO BE IMAGED | TUBE VOLTAGE (kV) | TUBE CURRENT (mA) | DOSE MEASUREMENT FIELD | IRRADIATION TIME (msec) | NECESSARY DOSE |
|---|---|---|---|---|---|
| ... | ... | ... | ... | ... | ... |
| CHEST AP | V1 | I1 | ▣ | t1' | X1 |
| CHEST PA | V2 | I2 | ▣ | t2' | X2 |
| ... | ... | ... | ... | ... | ... |

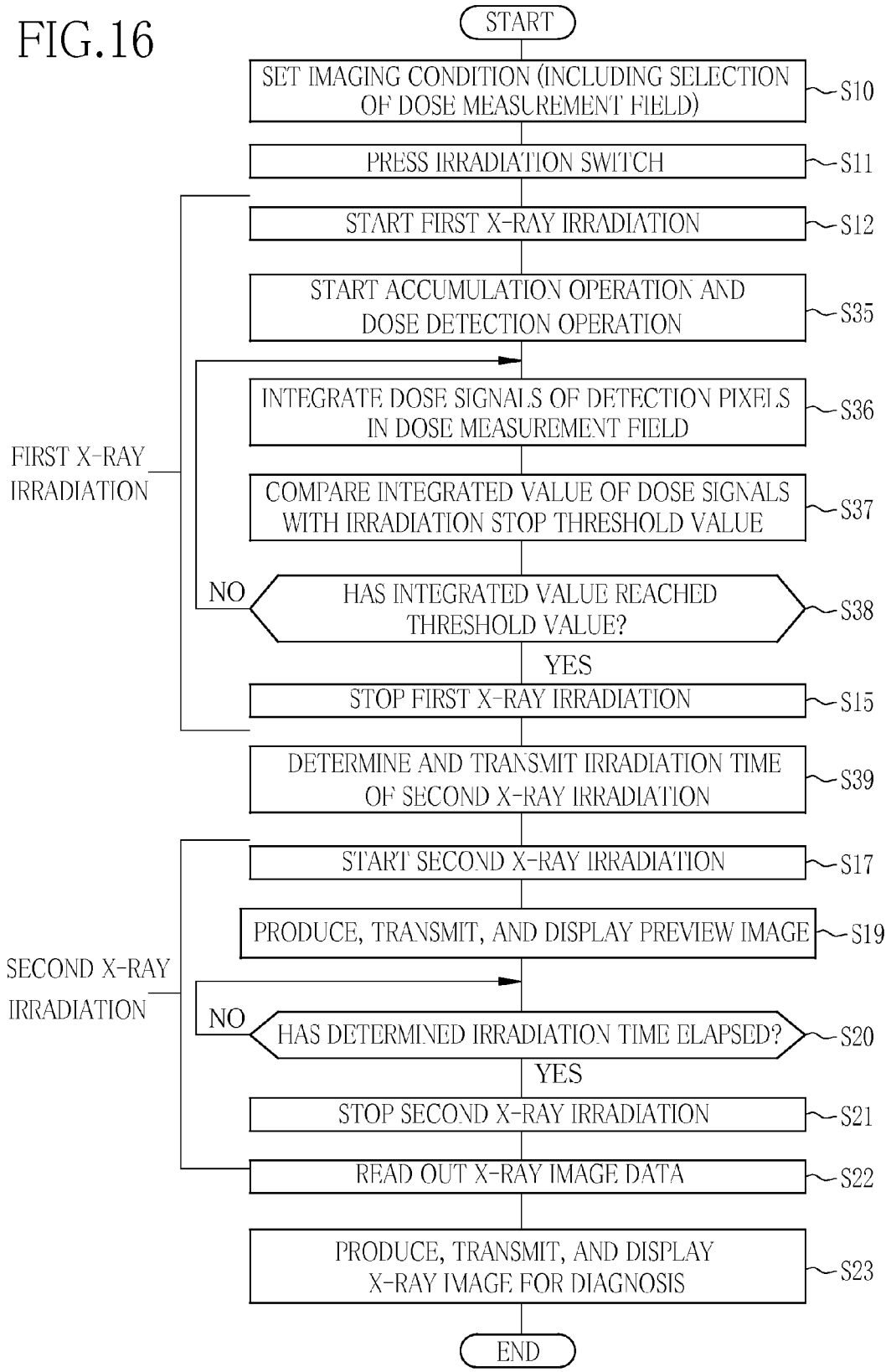

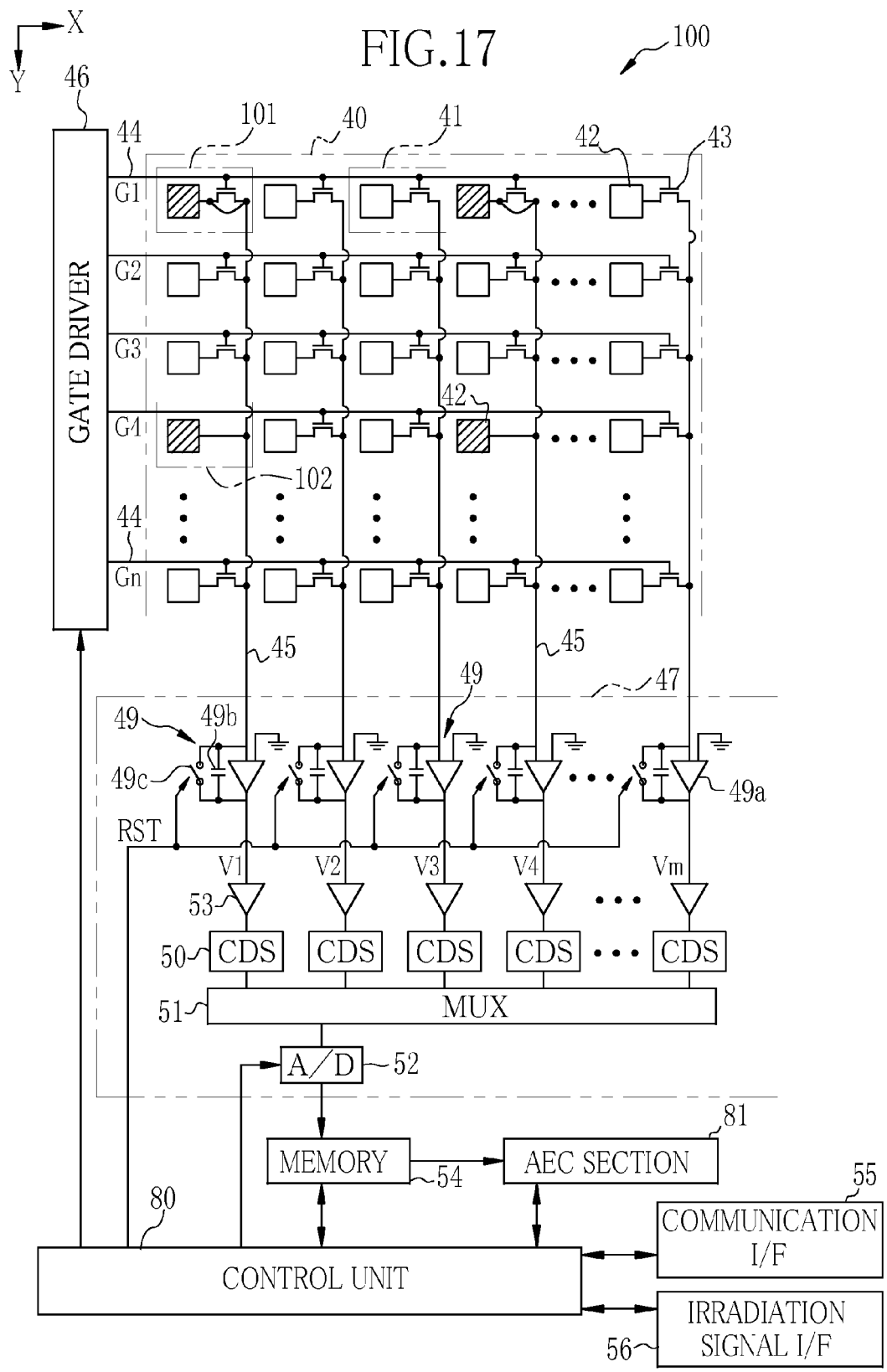

RADIATION IMAGING SYSTEM AND OPERATION METHOD THEREOF, AND RADIATION IMAGE DETECTING DEVICE AND STORAGE MEDIUM STORING OPERATION PROGRAM THEREFOR

CROSS-REFERENCE TO RELATED APPLICATIONS

This application is a Continuation of PCT International Application No. PCT/JP2013/073286 filed on Aug. 30, 2013, which claims priority under 35 U.S.C § 119(a) to Japanese Patent Application No. 2012-194582 filed Sep. 4, 2012. The above application is hereby expressly incorporated by reference, in its entirety, into the present application.

BACKGROUND OF THE INVENTION

1. Field of the Invention

The present invention relates to a radiation imaging system for acquiring a radiation image and an operation method thereof, and a radiation image detecting device and a storage medium storing an operation program therefor.

2. Description Related to the Prior Art

In a medical field, an X-ray imaging system using radiation such as X-rays is known, for example. The X-ray imaging system includes an X-ray generating apparatus for generating X-rays and an X-ray imaging apparatus for acquiring an X-ray image of an object (i.e. patient) from the X-rays having passed through the object. The X-ray generating apparatus includes an X-ray source for irradiating the X-rays to the object, a source controller for controlling the operation of the X-ray source, and an irradiation switch for inputting a command to start X-ray irradiation to the source controller. The X-ray imaging apparatus includes an X-ray image detecting device for detecting the X-ray image by converting the X-rays having passed through each part of the object into an electrical signal, and a console for controlling the operation of the X-ray image detecting device and storing and displaying the X-ray image.

An X-ray imaging apparatus using an X-ray image detecting device for electronically detecting an X-ray image has been widely spread instead of an X-ray image recording apparatus using an X-ray film or an imaging plate (IP) cassette. The X-ray image detecting device has a sensor panel that is also referred to as a flat panel detector (FPD).

The sensor panel has an imaging area in which pixels for accumulating signal charges corresponding to a dose of incident X-rays are arranged in a matrix form. Each of the pixels has a photoelectric converter for generating electric charges and accumulating the generated electric charges, and a switching element such as a thin film transistor (TFT). The sensor panel reads out the signal charges accumulated in the photoelectric converter of each of the pixels through a signal line disposed for each column of the pixels to a signal processing circuit upon turning-on of the switching element. Then, the signal charges are converted into a voltage signal in the signal processing circuit. Thereby, an X-ray image is electronically detected. The sensor panel performs an accumulation operation for accumulating the signal charges in each of the pixels, and a readout operation for reading out the accumulated signal charges through the switching element such as the TFT to the signal processing circuit.

As disclosed in United States Patent Application Publication No. 2012/132820 (corresponding to Japanese Patent Laid-Open Publication No. 2012-129984) and Japanese Patent Laid-Open Publication No. 2012-135588, in the case of acquiring one sheet of X-ray image, for example, a dose necessary for acquiring one sheet of X-ray image is set in accordance with a body part to be imaged and a body frame of an object in an X-ray generating apparatus. Then, when an irradiation switch is manipulated once by an operator such as a radiation technologist, the X-rays at the set dose are irradiated from the X-ray generating apparatus. In synchronization with the irradiation timing of the X-rays by the X-ray generating apparatus, the sensor panel turns off the switching element and performs an accumulation operation. Upon completion of the X-ray irradiation, the sensor panel turns on the switching element, and reads out the signal charges accumulated in the pixel to a signal processing circuit. Such a readout operation is performed for every pixel. After the readout operation, the sensor panel converts the signal charges into digital data by the signal processing circuit, so as to produce an X-ray image for diagnosis containing information of all pixels. The produced X-ray image for diagnosis is transmitted from the sensor panel to the console, and displayed on a monitor of the console.

An X-ray image detecting device disclosed in United States Patent Application Publication No. 2012/132820 and Japanese Patent Laid-Open Publication No. 2012-135588 includes a preview image producing device for subjecting the X-ray image for diagnosis to thinning processing so as to produce a preview image having a small amount of data. The produced preview image is transmitted to the console prior to transmission of the X-ray image for diagnosis. The preview image has a data amount smaller than that of the X-ray image for diagnosis, and therefore it takes a short period of time to transmit the preview image to the console. After the X-ray imaging, an operator measures success and failure of the X-ray imaging. For example, the operator checks whether or not the positioning of the object was appropriate on the monitor of the console. As disclosed in United States Patent Application Publication No. 2012/132820 and Japanese Patent Laid-Open Publication No. 2012-135588, in the case where the preview image is transmitted prior to transmission of the X-ray image for diagnosis, it becomes possible to measure success and failure of the X-ray imaging promptly.

According to United States Patent Application Publication No. 2012/132820 and Japanese Patent Laid-Open Publication No. 2012-135588, a series of processing including production, transmission, and display of the preview image is started after the X-ray irradiation necessary for acquiring one sheet of X-ray image is completed. The data transmission time to the console is shortened by producing the preview image having a small amount of data. However, since the above-described series of processing is started after the completion of the X-ray irradiation necessary for acquiring one sheet of X-ray image, it is impossible to make the time taken from the completion of the X-ray irradiation to the display of the preview image shorter than the time taken for the above-described series of processing. Although the waiting time before the preview image is displayed is a small amount of time, an operator who is required to perform an operation speedily feels like that the waiting time is long. Therefore, it has been desired strongly to decrease the time required for displaying the preview image. Consequently, it has been desired to take measures to display the preview image more promptly.

SUMMARY OF THE INVENTION

In view of the foregoing, an object of the present invention is to provide a radiation imaging system capable of decreasing time required for displaying a preview image and an operation method thereof, and a radiation image detecting device and a storage medium storing an operation program therefor.

To achieve the above and other objects of the present invention, a radiation imaging system according to the present invention includes a radiation source, a source controller, a radiation image detecting device, and a monitor. The radiation source irradiates radiation to an object. The source controller controls operation of the radiation source such that radiation is irradiated twice in performing radiography once to acquire one sheet of radiation image for diagnosis of the object. The radiation image detecting device detects the radiation image for diagnosis based on radiation having passed through the object. The monitor displays the radiation image. The radiation image detecting device further includes a data obtaining portion, a preview image producing portion, and an outputting portion. The data obtaining portion obtains data for producing a preview image to be displayed on the monitor prior to displaying the radiation image for diagnosis by first radiation irradiation. The preview image producing portion produces the preview image based on the data obtained by the data obtaining portion. The outputting portion starts output of the preview image produced by the preview image producing portion to the monitor before second radiation irradiation is finished.

The radiation imaging system further includes an irradiation switch for inputting a command to start radiation irradiation to the source controller. For example, the source controller makes the radiation source start the first radiation irradiation upon receiving the command to start radiation irradiation from the irradiation switch once, and makes the radiation source start the second radiation irradiation automatically after the first radiation irradiation is finished.

Preferably, the radiation image detecting device further includes a sensor panel having an imaging area in which pixels for accumulating electric charges corresponding to radiation dose are arranged, and a control unit for making the sensor panel perform an accumulation operation for accumulating the electric charges in the pixels and a readout operation for reading out the accumulated electric charges from the pixels.

The radiation image detecting device may be separate from the monitor. The outputting portion may be identical to a transmitting portion for transmitting the preview image to the monitor. The transmitting portion completes transmission of the preview image before the sensor panel starts the readout operation after the second radiation irradiation is finished. More specifically, the transmitting portion transmits the preview image while the sensor panel performs the accumulation operation in the second radiation irradiation.

The data obtaining portion preferably obtains data for producing the preview image from the sensor panel. In this case, the control unit makes the sensor panel perform the readout operation every time each of the first radiation irradiation and the second radiation irradiation is finished, and further makes the sensor panel output first image data corresponding to the first radiation irradiation and second image data corresponding to the second radiation irradiation. The preview image producing portion produces the preview image based on the first image data. For example, the preview image producing portion subjects the first image data to binning processing or thinning processing to produce the preview image.

The radiation image detecting device preferably has an image addition portion for adding up the first image data and the second image data to produce the radiation image for diagnosis.

The radiation image detecting device preferably includes a first body motion detecting portion for detecting presence or absence of body motion of the object in the first radiation irradiation and the second radiation irradiation based on a comparison result between the first image data and the second image data. The image addition portion does not operate in the case where the first body motion detecting portion detects body motion of the object. Additionally, the radiation imaging system may further include a warning section for displaying a warning in the case where body motion of the object is detected by the first body motion detecting portion.

The radiation image detecting device preferably includes a first imaging condition determining section for determining an irradiation time of the second radiation irradiation or a tube current-time product as a product of a tube current and an irradiation time, which is to be set in the source controller, as an item of an imaging condition for the second radiation irradiation based on the first image data.

Alternatively, the radiation image detecting device preferably includes a plurality of dose detection sensors each for detecting a dose of radiation reaching the imaging area in the first radiation irradiation and outputting a dose signal corresponding to the detected dose in order to perform exposure control of the radiation image for diagnosis.

The data obtaining portion obtains the data for producing the preview image from the dose detection sensors, and the preview image producing portion produces the preview image based the dose signal.

The control unit makes the sensor panel continue the accumulation operation during a period of time from when the first radiation irradiation is started to when the second radiation irradiation is finished, and further makes the sensor panel perform the readout operation after the second radiation irradiation is finished, so as to add up electric charges generated in the first radiation irradiation and electric charges generated in the second radiation irradiation in the pixels.

Each of the dose detection sensors preferably detects a dose more than once at least during the first radiation irradiation. Preferably, the radiation image detection device further includes a second body motion detecting portion for detecting presence or absence of body motion of the object based on a comparison result of the dose signals outputted from the dose detection sensors more than once, and the second body motion detecting portion outputs an irradiation stop signal for stopping the first radiation irradiation or the second radiation irradiation to the source controller in the case of detecting body motion of the object.

Preferably, some of pixels are used as the dose detection sensors. For example, as the pixels, there are normal pixels each of which accumulates signal charges upon receiving radiation and outputs the signal charges to a signal line in accordance with the operation of a switching element, and detection pixels each of which is driven separately from the normal pixel and provided with a switching element. The detection pixels are used as the dose detection sensors. The detection pixels, each of which is directly connected to the signal line in a short-circuited manner, or each of which is not provided with the switching element and directly connected to the signal line, may be used as the dose detection sensors.

Preferably, the radiation image detecting device includes a second imaging condition determining section for determining an irradiation time of the second radiation irradiation or a tube current-time product as a product of a tube current and an irradiation time, which is to be set in the source controller, as an item of an imaging condition for the second radiation irradiation based on the dose signal.

The preview image producing portion preferably subjects the radiation image for diagnosis to binning processing or thinning processing to produce a second preview image. Preferably, the outputting portion outputs the second preview image to the monitor after the second radiation irradiation is finished, and then outputs the radiation image for diagnosis which is not subjected to the binning processing or the thinning processing to the monitor.

The radiation image detecting device is preferably an electric cassette in which a sensor panel is contained in a portable housing.

An operation method according to the present invention is used for a radiation imaging system including a radiation source for irradiating radiation to an object, a source controller for controlling operation of the radiation source, and a radiation image detecting device for acquiring a radiation image of the object. In the operation method, the radiation detecting device is made to execute a data obtaining step, a preview image producing step, and an outputting step. The source controller controls operation of the radiation source such that radiation is irradiated twice in performing radiography once to acquire one sheet of radiation image for diagnosis of the object. In the data obtaining step, the radiation image detecting device obtains the data for producing a preview image to be displayed on a monitor prior to displaying the radiation image for diagnosis by the first radiation. In the preview image producing step, the preview image is produced based on the obtained data. In the outputting step, output of the produced preview image to the monitor is started before the second irradiation is finished.

Further, the radiation image detecting device according to the present invention is used for the radiation imaging system including a radiation source, a source controller, and a monitor. The radiation image detecting device includes a data obtaining portion, a preview image producing portion, and an outputting portion. The data obtaining portion obtains data for producing a preview image to be displayed on the monitor prior to displaying the radiation image for diagnosis by first radiation irradiation. The preview image producing portion produces the preview image based on the data obtained by the data obtaining portion. The outputting portion starts output of the preview image produced by the preview image producing portion to the monitor before second radiation irradiation is finished.

A storage medium according to the present invention stores an operation program for a radiation image detecting device which is readable by a computer, and the operation program includes a data obtaining step, a preview image producing step, and an outputting step. In the data obtaining step, data for producing a preview image to be displayed on the monitor prior to displaying the radiation image for diagnosis is obtained by first radiation irradiation. In the preview image producing step, the preview image is produced based on the data obtained by the data obtaining step. In the outputting step, output of the preview image produced by the preview image producing step to the monitor is started before second radiation irradiation is finished.

According to the present invention, radiation is irradiated twice in performing radiography once to acquire one sheet of radiation image for diagnosis, the preview image is produced based on the first X-ray irradiation, and output of the produced preview image to the monitor is started before the second X-ray irradiation is finished. Therefore, it is possible to display the preview image on the monitor before the second X-ray irradiation is finished and decrease the time required for displaying the preview image.

BRIEF DESCRIPTION OF DRAWINGS

For more complete understanding of the present invention, and the advantage thereof, reference is now made to the subsequent descriptions taken in conjunction with the accompanying drawings, in which:

FIG. 6 is a table showing imaging conditions set in a console;

FIG. 10 is a table showing imaging conditions set in a console according to a third embodiment;

FIG. 16 a flowchart showing a procedure for X-ray imaging according to a fourth embodiment; and FIG. 17 is a block diagram showing an internal structure of an electronic cassette provided with detection pixels as another example.

DESCRIPTION OF THE PREFERRED EMBODIMENTS

First Embodiment

Figure 1:
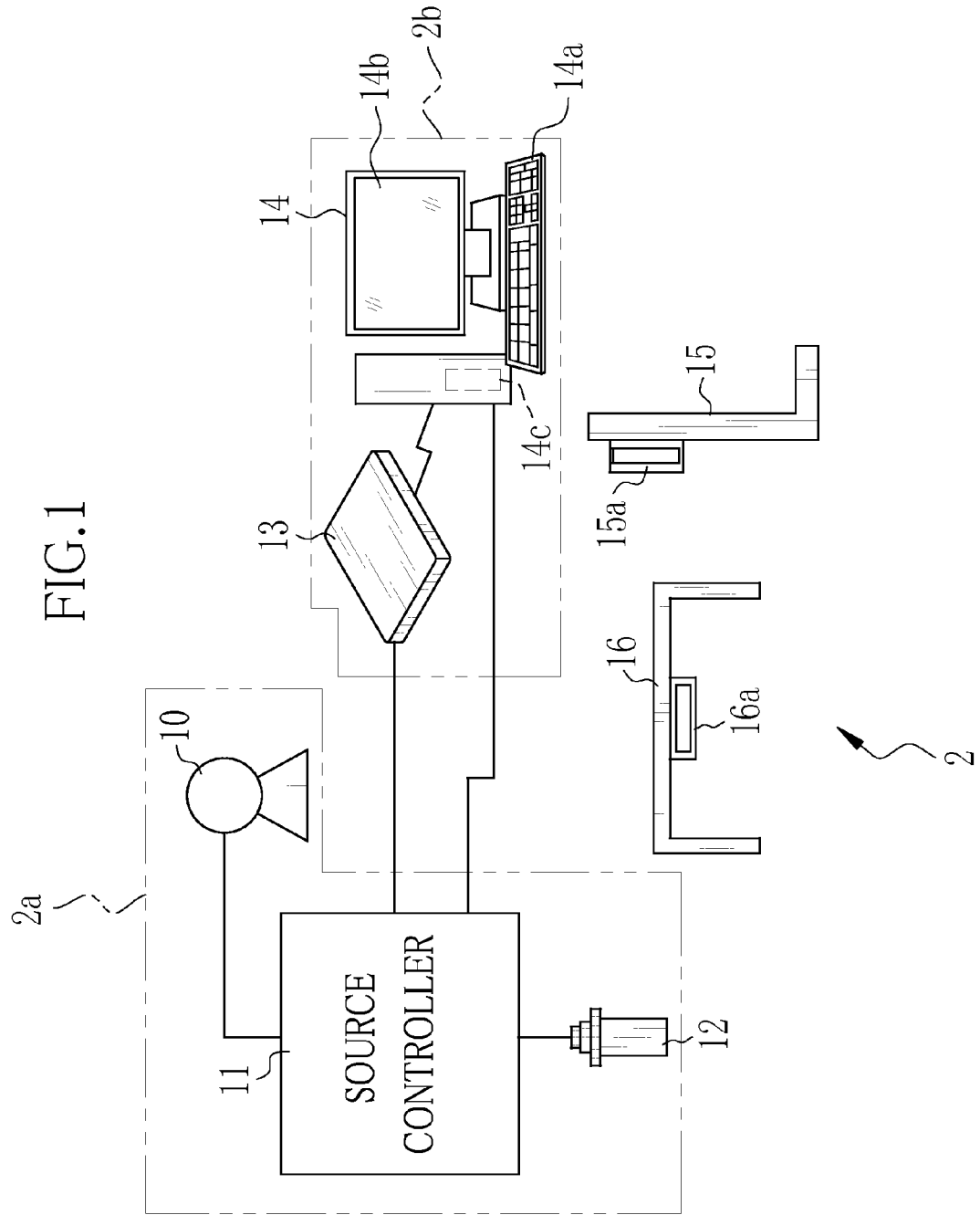
FIG. 1 is a schematic view showing an X-ray imaging system.

In FIG. 1, an X-ray imaging system 2 of the present invention includes an X-ray source 10 incorporating an X-ray tube for irradiating X-rays, a source controller 11 for controlling operation of the X-ray source 10, an irradiation switch 12 for giving a command to start warming-up and X-ray irradiation to the X-ray source 10, an electronic cassette 13 for detecting X-rays having passed through an object (i.e. patient) and outputting an X-ray image, a console 14 for performing operation control of the electronic cassette 13 and display processing of X-ray images, an upright-posture imaging table 15 for imaging the object in a standing posture, and a supine-posture imaging table 16 for imaging the object in a lying posture. The X-ray source 10, the source controller 11, and the irradiation switch 12 constitute an X-ray generating apparatus 2a. The electronic cassette 13 and the console 14 constitute an X-ray imaging apparatus 2b. Additionally, a source moving device (not shown in the drawing) is provided to set the X-ray source 10 in a desired direction and at a desired position. The X-ray source 10 is shared between the upright-posture imaging table 15 and the supine-posture imaging table 16.

The X-ray source 10 has the X-ray tube and an irradiation field limiter (collimator) for limiting an irradiation field of the X-rays to be irradiated from the X-ray tube. The X-ray tube has a cathode composed of a filament for emitting thermal electrons, and an anode (target) for irradiating the X-rays upon collision with the thermal electrons emitted from the cathode. The irradiation field limiter is composed of, for example, four lead plates for shielding the X-rays disposed on each side of a quadrangle, such that a quadrangular irradiation opening through which the X-rays pass is formed in the middle thereof. Shifting of the positions of the lead plates varies the size of the irradiation opening so as to limit the irradiation field.

The console 14 is communicably connected to the electronic cassette 13 in a wired manner or a wireless manner, and controls the operation of the electronic cassette 13 in response to input operation by an operator such as a radiation technologist through an input device 14a such as a keyboard. The X-ray image transmitted from the electronic cassette 13 is displayed on the monitor 14b of the console 14, and further, the data of the X-ray image is stored in a data storage. The data storage is, for example, a storage device 14c or a memory in the console 14, or an image storage server connected to the console 14 through a network.

The console 14 receives the input of an examination order containing information relating to the sex, age, body part to be imaged, and imaging objective of each object, and displays the examination order on the monitor 14b. The examination order is inputted from an external system, such as hospital information system (HIS) or radiation information system (RIS), which manages patient information and examination information relating to radiographic examination. Alternatively, the examination order is inputted manually by an operator such as a radiation technologist. Items regarding the body part to be imaged, such as head, chest, abdomen, hand, and finger, are contained in the examination order. Additionally, the body part to be imaged contains an imaging direction such as front, side, oblique, PA (in which X-rays are irradiated from the rear of the object), and AP (in which X-rays are irradiated from the front of the object). The operator confirms the details of the examination order on the monitor 14b, and inputs an imaging condition corresponding to the details of the examination order through the operation screen displayed on the monitor 14b using the input device 14a.

In the X-ray imaging system 2, the X-rays are irradiated twice in performing X-ray imaging once, to acquire one sheet of X-ray image for use in diagnosis (i.e. X-ray image for diagnosis). After the first X-ray irradiation is finished, a preview image is produced based on a first image data detected after the first X-ray irradiation is finished in the electronic cassette 13. The preview image is used by the operator to measure success and failure of the X-ray imaging. For example, the operator checks whether or not the positioning of the object and the body part of the object to be imaged were appropriate. Accordingly, in the preview image, the object may be visualized to an extent that makes it possible to measure success and failure of the X-ray imaging. Therefore, in the first X-ray irradiation, the dose of X-rays to be irradiated is enough as long as the preview image performs its function. Further, the first image data obtained by the first X-ray irradiation is also utilized to acquire one sheet of X-ray image for diagnosis. Therefore, the dose in the first X-ray irradiation is subtracted from a dose necessary for acquiring one sheet of X-ray image, and the X-rays corresponding to the dose obtained by the subtraction is irradiated in the second X-ray irradiation.

Figure 2:
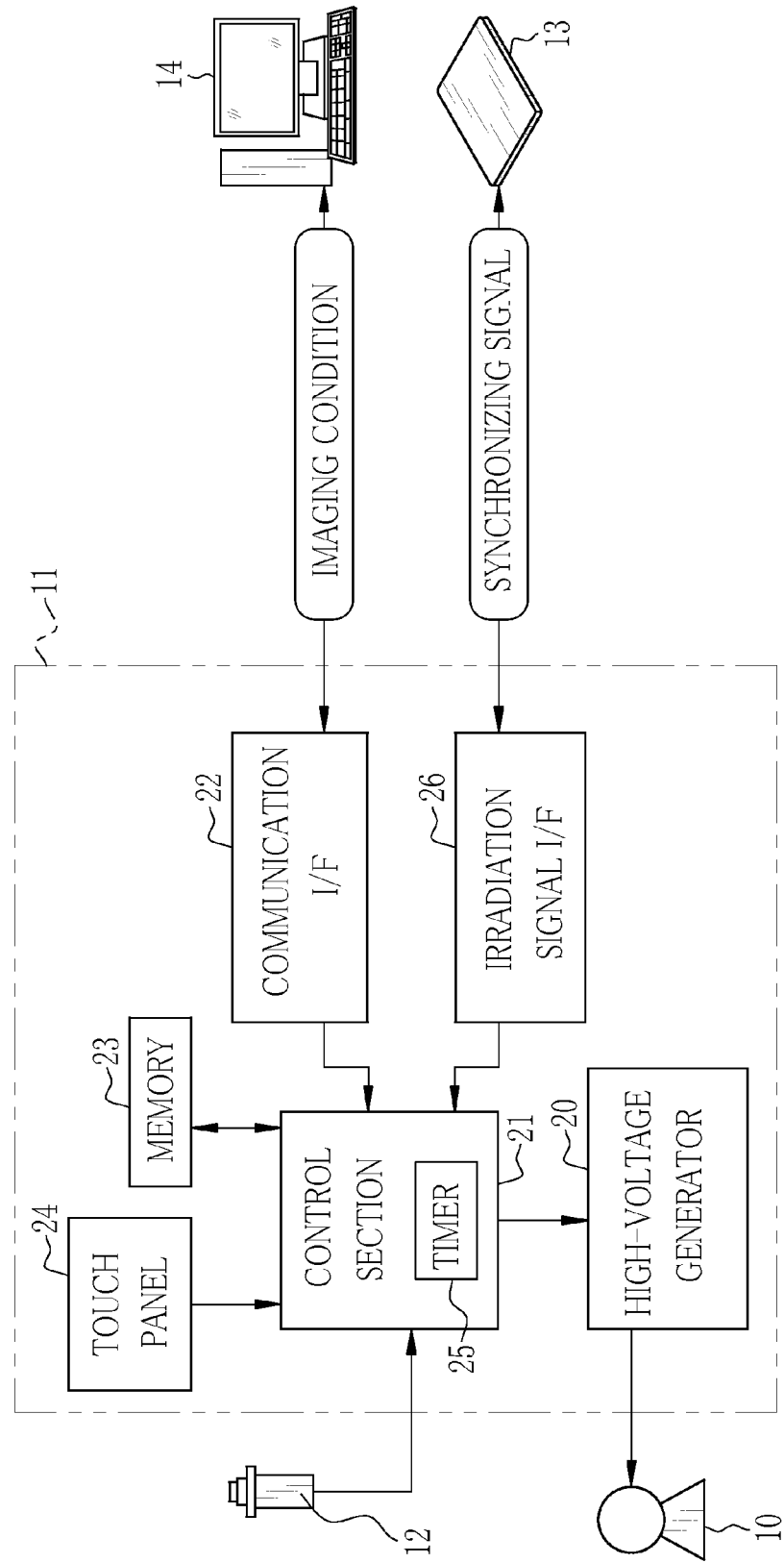
FIG. 2 is a view showing an internal structure of a source controller.

As shown in FIG. 2, the source controller 11 includes a high-voltage generator 20, a control section 21, and a communication I/F 22. The high-voltage generator 20 generates a high tube voltage by multiplying an input voltage using a transformer, and supplies the high tube voltage to the X-ray source 10 through a high voltage cable. The control section 21 controls the tube voltage for determining a radiation quality (i.e. energy spectrum) of the X-rays to be irradiated from the X-ray source 10, a tube current for determining the dose of the X-rays per unit of time, and the irradiation time of the X-rays. The communication I/F 22 mediates transmission and reception of essential information to and from the console 14.

The irradiation switch 12, a memory 23, and a touch panel 24 are connected to the control section 21. The irradiation switch 12 is a two-step push-button switch for inputting a command to start the X-ray irradiation to the control section 21. An operation signal from the irradiation switch 12 is inputted through a signal cable to the control section 21. Upon halfway pressing of the irradiation switch 12, the control section 21 issues a warming-up start signal to the high-voltage generator 20 so as to start warming-up of the X-ray source 10. Upon full pressing of the irradiation switch 12, the control section 21 issues an irradiation start signal to the high-voltage generator 20 so as to start the X-ray irradiation from the X-ray source 10.

Although the X-ray generating apparatus 2a irradiates the X-rays twice in performing the X-ray imaging once, the irradiation switch 12 is manipulated once for each X-ray imaging. Specifically, upon full pressing of the irradiation switch 12 once, the control section 21 starts the first X-ray irradiation, and after completion of the first X-ray irradiation, the control section 21 automatically starts the second X-ray irradiation. Upon cancellation of the full pressing of the irradiation switch 12 in the middle of the X-ray irradiation, the control section 21 urgently stops the X-ray irradiation from the X-ray source 10.

The memory 23 stores the imaging conditions such as the tube voltage, the tube current, and the irradiation time set in the console 14. The touch panel 24 is used for the setting of the source controller 11. The source controller 11 receives the imaging condition through the communication I/F 22 from the console 14. The control section 21 stores the received imaging condition in the memory 23. The control section 21 incorporates a countdown timer (timer) 25 used for stopping the X-ray irradiation when the set irradiation time has elapsed.

The irradiation signal I/F 26 is connected to the electronic cassette 13 in a wired manner or in a wireless manner. Upon the halfway pressing of the irradiation switch 12, the control section 21 starts warming up the X-ray source 10, and transmits an irradiation start request signal for inquiring whether or not to permit the start of X-ray irradiation through the irradiation signal I/F 26 to the electronic cassette 13.

Upon receiving the irradiation start request signal, the electronic cassette 13 checks whether or not the electronic cassette 13 itself is ready for the X-ray imaging. In the case where the electronic cassette 13 stands ready, the electronic cassette 13 issues an irradiation permission signal. In the case where the irradiation switch 12 is fully pressed and the control section 21 receives the irradiation permission signal through the irradiation signal I/F 26, the control section 21 makes the high-voltage generator 20 start supplying electricity to the X-ray source 10 so as to perform the first X-ray irradiation. Furthermore, when it is determined that the irradiation time set for each of the first X-ray irradiation and the second X-ray irradiation has elapsed by the timer 25, the control section 21 issues an irradiation stop signal for stopping the X-ray irradiation through the irradiation signal I/F 26 to the electronic cassette 13, and makes the high-voltage generator 20 stop supplying electricity to the X-ray source 10 so as to stop the X-ray irradiation. The irradiation start request signal, irradiation permission signal, and irradiation stop signal are synchronizing signals to be used for synchronization control of the source controller 11 and the electronic cassette 13. The synchronizing signals are transmitted/received in each of the first X-ray irradiation and the second X-ray irradiation.

Figure 3:
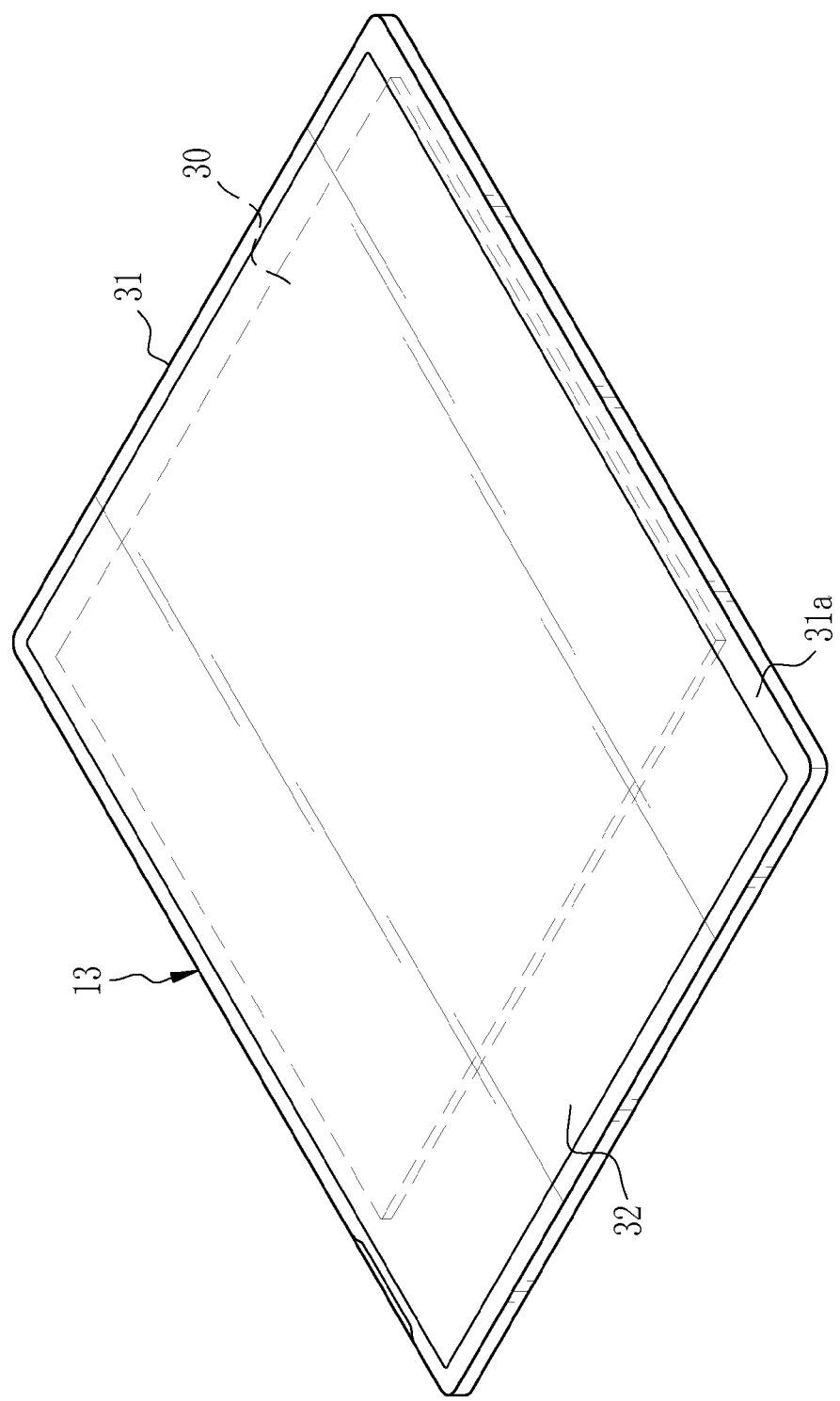
FIG. 3 is a perspective view showing an external appearance of an electronic cassette.

In FIG. 3, the electronic cassette 13 consists of a sensor panel 30 and a flat box-shaped portable housing 31 for containing the sensor panel 30. The housing 31 is formed from a conductive resin, for example. A front surface 31a of the housing 31, through which the X-rays enter, has an opening having a rectangular shape. A transparent plate 32 as a top panel is attached to the opening. The transparent plate 32 is formed from a carbon material that is lightweight and has high rigidity and high X-ray transparency. The housing 31 also functions as an electromagnetic shield for preventing electromagnetic noise from entering the electronic cassette 13 and for preventing electromagnetic noise from being emitted from the electronic cassette 13 to the outside. Note that, the housing 31 incorporates not only the sensor panel 30 but also a battery (secondary battery) for supplying electricity at a predetermined voltage to the respective components of the electronic cassette 13 and an antenna for use in wireless communication of data such as the X-ray images with the console 14.

The housing 31 has approximately the same size as those of a film cassette and an IP cassette. The size of the housing 31 is compatible with International Standard ISO 4090: 2001. Therefore, the electronic cassette 13 is detachably set to a holder 15a of the upright-posture imaging table 15 or a holder 16a of the supine-posture imaging table 16 (see FIG. 1), respectively, such that the front surface 31a of the housing 31 is held in a posture facing the X-ray source 10. Then, the X-ray source 10 is moved by the source moving device depending on the imaging table to be used. Further, in some cases, the electronic cassette 13 is put on a bed on which the object is lying, or held by the object itself, to be used solely, in stead of being set to the imaging table 15 or 16. Note that, since the electronic cassette 13 has approximately the same size as those of the film cassette and the IP cassette, the electronic cassette 13 can be set to an existing imaging table designed for the film cassette and the IP cassette.

Figure 4:
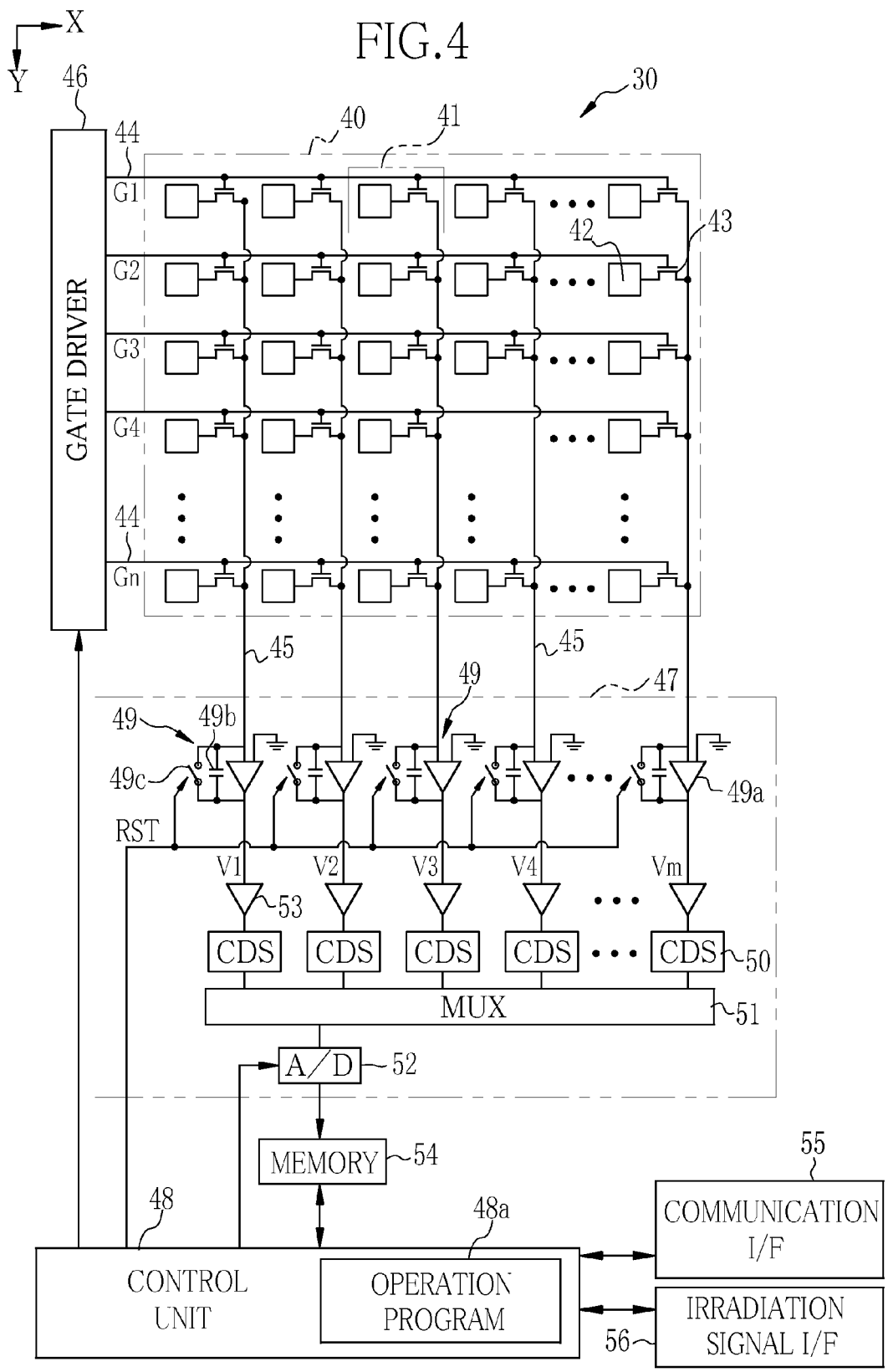
FIG. 4 is a block diagram showing an internal structure of the electronic cassette.

The electronic cassette 13 includes the sensor panel 30 as an image detecting section and a control unit 48 for controlling operation of the sensor panel 30, as shown in FIG. 4. The sensor panel 30 has a TFT active matrix substrate on which an imaging area 40 is formed. On the imaging area 40, a plurality of pixels for accumulating electric charges corresponding to the received X-ray dose are arranged in a matrix form with n rows (that is along X direction) and m columns (that is along Y direction) at a predetermined pitch. Note that, each of n and m is an integer of two or more.

The sensor panel 30 has a scintillator (i.e. a phosphor, not shown in the drawing) for converting the X-rays into visible light. The sensor panel 30 is of an indirect-conversion type in which the visible light obtained by converting the X-rays by the scintillator is photoelectrically converted in the pixels 41. The scintillator is made of CsI:Tl (thallium activated cesium iodide), GOS ($Gd_2O_2S$:Tb, terbium activated gadolinium oxysulfide), or the like, and is opposed to the entire surface of the imaging area 40 on which the pixels 41 are arranged. Note that, the scintillator and the TFT active matrix substrate may be disposed according to either a Penetration Side Sampling (PSS) system in which the scintillator and the substrate are disposed in this order from the X-ray incident side, or an irradiation side sampling (ISS) system in which the substrate and the scintillator are disposed in this order from the X-ray incident side, in contrast to the PSS system. Alternatively, a sensor panel of a direct-conversion type, which has a conversion layer (amorphous selenium or the like) for directly converting the X-rays into the electric charges without using the scintillator, may be used instead.

As well known, each of the pixels 41 includes a photoelectric converter 42 for generating the electric charges (electron-hole pairs) upon incidence of the visible light and accumulating the generated electric charges, and a TFT 43 as a switching element. Note that, a capacitor for accumulating the electric charges may be provided separately from the photoelectric converter 42.

Each of the photoelectric converters 42 has a structure in which a semiconductor layer (for example, of a PIN (p-intrinsic-n) type) for generating electric charges is sandwiched between an upper electrode and a lower electrode. The TFT 43 is connected to the lower electrode of the photoelectric converter 42, and a bias line is connected to the upper electrode of the photoelectric converter 42. The number of the bias lines corresponds to the number of rows (n rows) of the pixels 41, and the bias lines are coupled to a single bus. The bus is connected to a bias power supply. A bias voltage is applied from the bias power supply to the upper electrode of each of the photoelectric converters 42 through the bus and the bias line as a subordinate of the bus. With the application of the bias voltage, an electric field is generated in the semiconductor layer, and the electric charges (electron-hole pairs) generated in the semiconductor layer by photoelectric conversion are moved to the upper electrode and the lower electrode, one of which has positive polarity, and the other of which has negative polarity. Thereby, the electric charges are accumulated in the photoelectric converters 42.

Each of the TFTs 43 has a gate electrode connected to a scanning line 44, a source electrode connected to a signal line 45, and a drain electrode connected to the photoelectric converter 42. The scanning lines 44 and the signal lines 45 are wired in a lattice shape. The number of the scanning lines 44 corresponds to the number of rows (n rows) of the pixels 41, such that one scanning line 44 is provided for the pixels 41 arranged in one row. Further, the number of the signal lines 45 corresponds to the number of columns (m columns) of the pixels 41, such that one signal line 45 is provided for the pixels 41 arranged in one column. The scanning lines 44 are connected to a gate driver 46, and the signal lines 45 are connected to a signal processing circuit 47.

Under the control of the control unit 48, the gate driver 46 drives the TFTs 43, such that the sensor panel 30 carries out an accumulation operation for accumulating the signal charges corresponding to the received X-ray dose in the pixels 41, a readout operation for reading out the signal charges accumulated in the pixels 41, and a reset operation. In the accumulation operation, the signal charges are accumulated in the pixels 41 while the TFTs 43 are turned off. In the readout operation, the gate driver 46 sequentially issues gate pulses G1 to Gn, each of which drives the TFTs 43 in the corresponding row at a time, at a predetermined time interval. Thereby, the scanning lines 44 are activated sequentially on a row-by-row basis, such that the TFTs 43 connected to the activated scanning lines 44 are turned on sequentially on a row-by-row basis. When the TFT 43 is turned on, the electric charges accumulated in the photoelectric converter 42 of each of the pixels 41 are read out to the signal line 45, and inputted to the signal processing circuit 47.

Dark charges are generated in the semiconductor layer of each of the photoelectric converters 42 irrespective of incidence of the X-rays. Due to the application of the bias voltage, the dark charges are accumulated in the photoelectric converter 42 of each of the pixels 41. The dark charges generated in the pixels 41 become noise components in the image data, and therefore the reset operation is carried out at a predetermined time interval so as to remove the dark charges before the X-ray irradiation is started. The reset operation is carried out to discharge the dark charges generated in the pixels 41 through the signal lines 45.

The reset operation is carried out by a sequential reset method, for example, by which the pixels 41 are reset on a row-by-row basis. In the sequential reset method, as with the readout operation of the signal charges, the gate driver 46 sequentially issues the gate pulses G1 to Gn to the scanning lines 44 at a predetermined time interval so as to turn on the TFTs 43 on a row-by-row basis.

Instead of the sequential reset method, a parallel reset method or an all-pixels reset method may be used. In the parallel reset method, a plurality of rows of pixels are grouped together, and the reset operation is sequentially carried out in each of the groups, so as to concurrently discharge the dark charges from the rows corresponding to the number of the groups. In the all-pixels reset method, the gate pulse is inputted to every row to discharge the dark charges from every pixel at a time. The parallel reset method and the all-pixels reset method enable the speeding up of the reset operation.

The signal processing circuit 47 includes integration amplifiers 49, correlated double sampling (CDS) circuits 50, a multiplexer (MUX) 51, an A/D converter (A/D) 52, and the like. The integration amplifier 49 is connected one-by-one to each of the signal lines 45. Each of the integration amplifiers 49 consists of an operational amplifier 49a and a capacitor 49b connected between input and output terminals of the operational amplifier 49a. The signal line 45 is connected to one of input terminals of the operational amplifier 49a. The other one of the input terminals of the operational amplifier 49a is connected to a ground (GND). To the capacitor 49b, a reset switch 49c is connected in parallel. Each of the integration amplifiers 49 integrates the electric charges inputted thereto through the signal line 45, converts the electric charges into analog voltage signals V1 to Vm, and outputs the analog voltage signals V1 to Vm. An output terminal of the operational amplifier 49a in each column is connected to the MUX 51 through an amplifier 53 and the CDS circuit 50. The A/D 52 is connected to the output side of the MUX 51.

The CDS circuit 50, each having a sample-and-hold circuit, applies correlated double sampling to the output voltage signal from the integration amplifier 49 so as to remove the noise components therefrom, and holds the output voltage signal from the integration amplifier 49 in the sample-and-hold circuit for a predetermined period of time (i.e. performs sample holding). The MUX 51 sequentially selects one of the CDS circuits 50 connected in parallel from every row with use of an electronic switch based on an operation control signal from a shift resister (not shown in the drawing), such that the voltage signals V1 to Vm outputted from the selected CDS circuits 50 are serially inputted to the A/D 52. Further, another amplifier may be connected between the MUX 51 and the A/D 52.

The A/D 52 converts the inputted analog voltage signals V1 to Vm corresponding to one row into a digital value, and outputs the digital value to a memory 54 contained in the electronic cassette 13. The memory 54 stores the digital value corresponding to one row in association with coordinate of each of the pixels 41 as image data of the X-ray image corresponding to one row. Thereby, the readout operation corresponding to one row is completed.

After the MUX 51 reads out the voltage signals V1 to Vm corresponding to one row from the integration amplifiers 49, the control unit 48 outputs a reset pulse RST to the integration amplifiers 49, such that the reset switches 49c are turned on. Thereby, the signal charges corresponding to one row accumulated in the capacitors 49b are discharged, and the integration amplifiers 49 are reset. After the integration amplifiers 49 are reset, the reset switches 49c are turned off again. After a lapse of a predetermined period of time from the turning off of the reset switches 49c, one of the sample-and-hold circuits in each of the CDS circuits 50 is held so as to sample a kTC noise component of the integration amplifier 49. Thereafter, the gate pulse corresponding to the next row is outputted from the gate driver 46 so as to start reading out the signal charges from the pixels 41 of the next row. After a lapse of a predetermined period of time from the outputting of the gate pulse, the signal charges of the pixels 41 of the next row are held by another one of the sample-and-hold circuits in each of the CDS circuits 50. By repetition of the above operation, the signal charges are read out from the pixels 41 of every row.

After the completion of the readout operation from every row, the image data representing the X-ray image within a single screen is stored in the memory 54. The sensor panel 30 carries out the accumulation operation in accordance with the timing of starting X-ray irradiation from the X-ray source 10 in each of the first X-ray irradiation and the second X-ray irradiation. Upon completion of each of the first X-ray irradiation and the second X-ray irradiation, the sensor panel 30 carries out the readout operation. Accordingly, a first image data which is read out after the first X-ray irradiation is finished and the second image data which is read out after the second X-ray irradiation is finished are respectively stored in the memory 54. The first image data and the second image data are read out from the memory 54, and subjected to various types of image processing in the control unit 48. The control unit 48 produces a preview image based on the first image data, and further produces an X-ray image for diagnosis based on the first image data and the second image data. As described above, the control unit 48 obtains the first image data and the second image data. Specifically, the control unit 48 functions as a data obtaining portion for obtaining data for producing the preview image.

Note that, in the reset operation, while the TFTs 43 are turned on, the dark charges from the pixels 41 flow into the capacitors 49b of the integration amplifiers 49 through the signal lines 45. In contrast to the readout operation, the MUX 51 does not read out the electric charges accumulated in the capacitors 49b, and in synchronization with the issue of each of the gate pulses G1 to Gn, the control unit 48 outputs the reset pulse RST. Thereby, the reset switches 49c are turned on, and the electric charges accumulated in the capacitors 49b are discharged, such that the integration amplifiers 49 are reset.

The irradiation signal I/F 26 of the source controller 11 is connected to an irradiation signal I/F 56 in a wired or wireless manner. The irradiation signal I/F 56 mediates transmission and reception of the synchronizing signal to and from the source controller 11. Specifically, the irradiation signal I/F 56 mediates reception of the irradiation start request signal, transmission of the irradiation permission signal in response to the irradiation start request signal, and reception of the irradiation stop signal.

An operation program 48a is stored in the control unit 48. Upon execution of the operation program 48a, various functions shown in FIG. 5 are established in the control unit 48.

Figure 5:
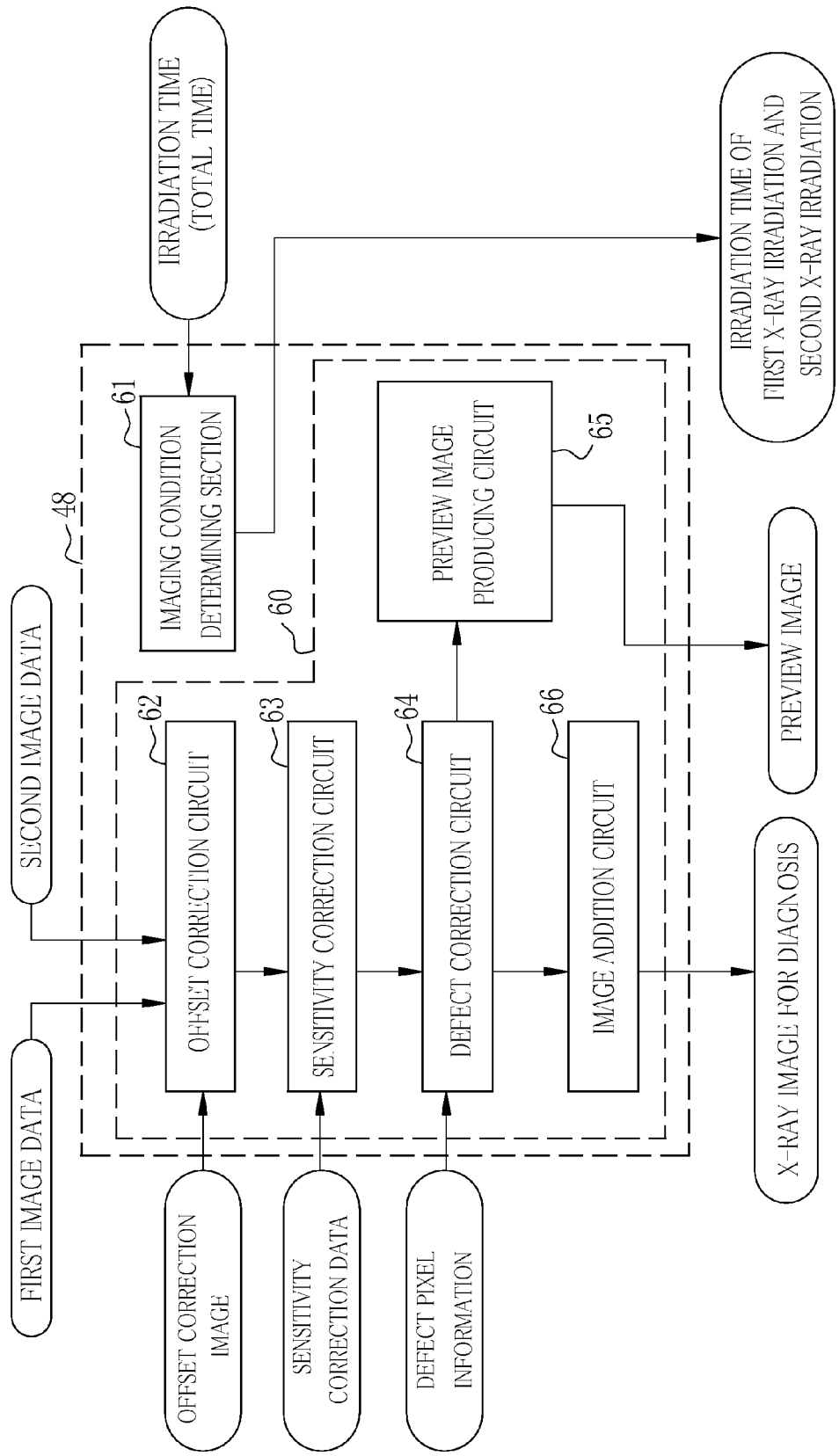
FIG. 5 is a block diagram showing an internal structure of a control unit of the electronic cassette.

In FIG. 5, the control unit 48 includes an image processing section 60 and an imaging condition determining section 61. The image processing section 60 includes an offset correction circuit 62 for subjecting each of the first image data and the second image data stored in the memory 54 to offset correction, a sensitivity correction circuit 63 for subjecting each of the first image data and the second image data stored in the memory 54 to sensitivity correction, a defect correction circuit 64 for subjecting each of the first image data and the second image data stored in the memory 54 to defect correction, a preview image producing circuit 65, and an image addition circuit 66 (corresponding to an image addition portion). The offset correction circuit 62 subtracts an offset correction image, which is obtained from the sensor panel 30 without irradiation of the X-rays, from the X-ray image on a pixel-by-pixel basis, in order to remove fixed pattern noise caused by the individual difference of the signal processing circuit 47 and imaging environment. The sensitivity correction circuit 63, which is also called as a gain correction circuit, corrects variations in the sensitivity of the photoelectric converter 42 of each of the pixels 41, variations in the output property of the signal processing circuit 47, and the like. The defect correction circuit 64 performs linear interpolation of a pixel value of a defect pixel using a pixel value of a normal pixel around the defect pixel, based on defect pixel information produced at the time of shipping or periodic inspection. After the various types of correction processing, the correction circuits 62 to 64 respectively store the processed first and second image data in the memory 54.

The preview image producing circuit 65 reads out the first image data subjected to the various types of correction processing from the memory 54, and applies binning processing or thinning processing to the first image data so as to produce the preview image. In the binning processing, a plurality of adjacent pixels arranged in two rows and two columns, three rows and three columns, or the like are grouped as one pixel, pixel values of the plurality of adjacent pixels are added up, and the additional value is considered as a representative pixel value of the plurality of adjacent pixels. In the thinning processing, the pixel value is thinned in a predetermined row or column, or at each predetermined position. Note that, the preview image is used to measure success and failure of the X-ray imaging, and it is sufficient that a certain level of image quality is achieved by the preview image. Therefore, the preview image may be produced based on the first image before being subjected to the various types of correction processing.

After producing the preview image, the control unit 48 transmits the preview image through a communication I/F 55 to the console 14. Here, the control unit 48 functions as a transmitting portion for transmitting the preview image through the communication I/F 55 to the console 14 having the monitor 14b. The timing for transmitting the preview image is before the second X-ray irradiation is finished (namely, before the accumulation operation performed by the sensor panel 30 in response to the second X-ray irradiation is finished). It is because, in the case where the preview image is transmitted while the sensor panel 30 reads out the second image data after the second X-ray irradiation is finished, communication noise may be added to the second image data read out by the sensor panel 30 and thus the image quality may be deteriorated. More preferable timing for transmitting the preview image is a period of time between the start and completion of the second X-ray irradiation, namely, during the accumulation operation in response to the second X-ray irradiation. During the period of time between the completion of the first X-ray irradiation and the start of the second X-ray irradiation, transmission and reception of the irradiation start request signal and the irradiation permission signal to and from the source controller 11 are performed. Therefore, in the case where the transmission of the preview image is performed during the above-described period of time, load due to the processing applied to the control unit 48 is increased, and thus retardation may occur in transmission and reception of the synchronizing signals to and from the source controller 11.

The image addition circuit 66 reads out the first and second image data which have been subjected to various types of image processing from the memory 54, and adds up the pixel values of the pixels at the corresponding coordinates based on the first and second image data, so as to produce the X-ray image for diagnosis.

The imaging condition determining section 61 receives information of the imaging conditions set in the console 14 through the communication I/F 55, and determines the irradiation time of the first X-ray irradiation and the irradiation time of the second X-ray irradiation.

The console 14 stores imaging conditions for the respective body parts to be imaged in advance as shown in FIG. 6. The imaging conditions include tube voltage (unit; kV), tube current (unit; mA), and an irradiation time (unit; msec). The irradiation time corresponds to a dose necessary for the X-ray image for diagnosis having an appropriate image quality. The dose of X-rays is obtained based on a tube current-time product (mAs value) as a product of the tube current and the irradiation time. Therefore, in the case where the tube current is identified, the irradiation time for obtaining the necessary dose is also identified. The information of the imaging conditions is stored in the storage device 14c. The imaging condition corresponding to the body part to be imaged, which is specified by the input device 14a, is read out from the storage device 14c, and transmitted through the communication I/F 55 to the electronic cassette 13.

The irradiation time received by the electronic cassette 13 from the console 14 is a total time corresponding to the dose necessary for performing X-ray imaging once. The ratio of dose allocated between the first X-ray irradiation and the second X-ray irradiation is preliminarily set in the imaging condition determining section 61 (in which 10% of the dose is allocated to the first X-ray irradiation, and 90% of the dose is allocated to the second X-ray irradiation, for example). The imaging condition determining section 61 allocates the irradiation time received from the console 14 to the first X-ray irradiation and the second X-ray irradiation based on the dose ratio, so as to determine the irradiation time of each of the first and second X-ray irradiation.

The imaging condition determining section 61 transmits the information of the irradiation time of each of the first and second X-ray irradiation determined as described above through the communication I/F 55 to the console 14. Further, the console 14 transmits the received information of the irradiation time of each of the first and second X-ray irradiation to the source controller 11.

Figure 7:
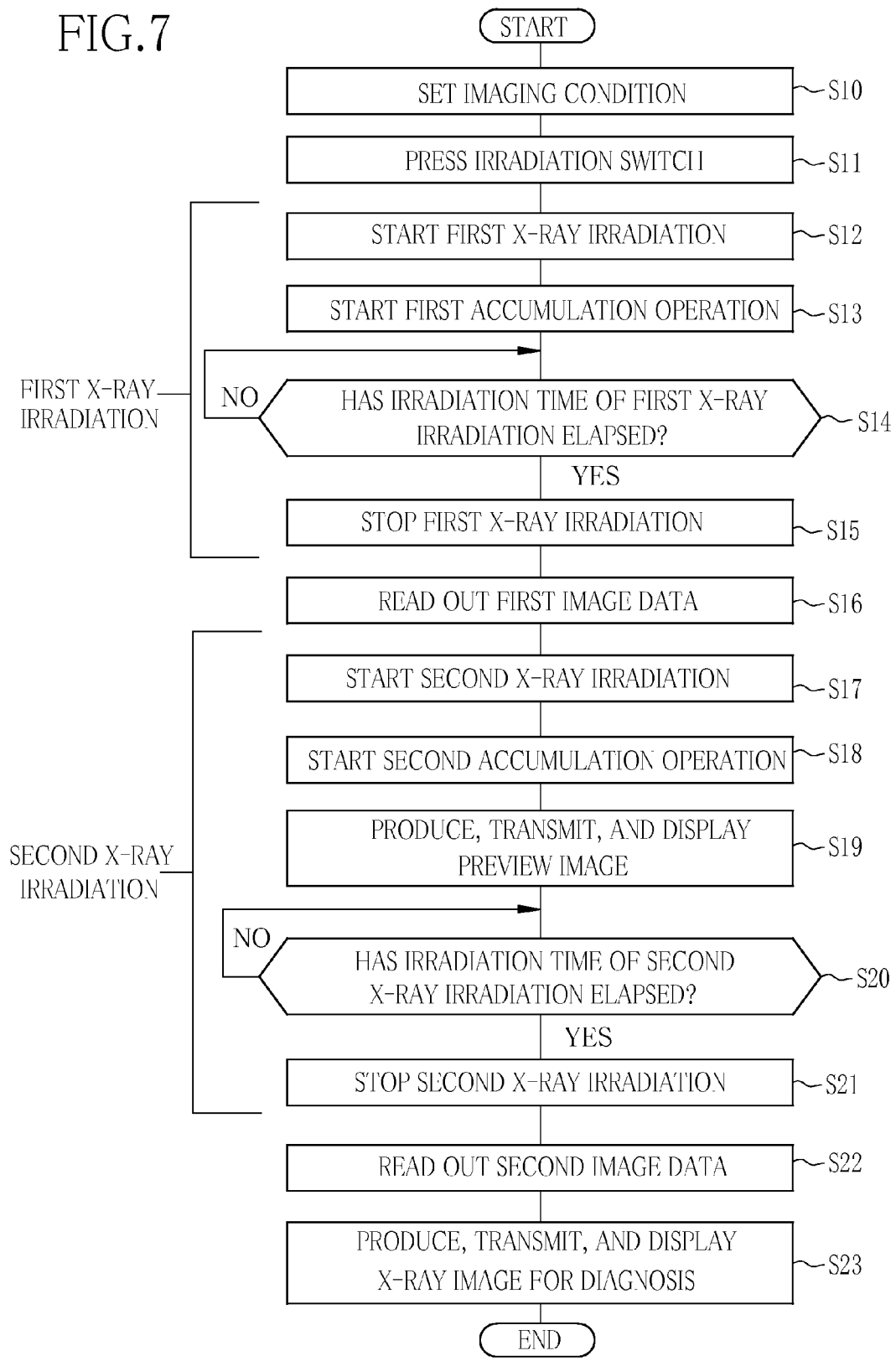
FIG. 7 is a flowchart showing a procedure for X-ray imaging.

Next, with reference to a flowchart in FIG. 7, the procedure for performing X-ray imaging once through the first X-ray irradiation and the second X-ray irradiation in the X-ray imaging system 2 is explained.

At first, the object is set to a predetermined imaging position on one of the upright-posture imaging table 15 and the supine-posture imaging table 16, and positioning is performed by adjusting a height and a horizontal position of the electronic cassette 13 to the body part of the object to be imaged. Then, a height and a horizontal position of the X-ray source 10, and a size of the irradiation field of the X-rays from the X-ray source 10 are adjusted in accordance with the position of the electronic cassette 13 and the size of the body part to be imaged. Next, the imaging condition is set in the console 14 (step S10). The imaging condition set in the console 14 is provided to the electronic cassette 13.

The imaging condition determining section 61 determines the irradiation time of each of the first and second X-ray irradiation based on the irradiation time contained in the imaging condition received from the console 14, and returns the irradiation time of each of the first and second X-ray irradiation to the console 14. The console 14 transmits the tube current, the tube voltage, and the irradiation time of each of the first and second X-ray irradiation determined by the imaging condition determining section 61 as the items of the imaging condition to the source controller 11. The source controller 11 stores the received imaging condition in the memory 23 so as to complete the setting of the imaging condition.

Upon completion of the setting of the imaging condition, the operator presses the irradiation switch 12 (step S11). Upon the halfway pressing of the irradiation switch 12, the source controller 11 makes the X-ray source 10 start warming up. Further, transmission and reception of the irradiation start request signal and the irradiation permission signal as the synchronizing signals are performed between the source controller 11 and the electronic cassette 13. Upon the full pressing of the irradiation switch 12, the source controller 11 makes the X-ray source 10 start the first X-ray irradiation (step S12).

On the other hand, in a standby mode before the X-ray imaging, the sensor panel 30 repeats the reset operation. In accordance with transmission and reception of the synchronizing signals to and from the source controller 11, the sensor panel 30 finishes the reset operation and starts the accumulation operation. In other words, the sensor panel 30 shifts from the standby mode to an imaging mode (step S13). In the imaging mode, upon receiving the first X-ray irradiation, the sensor panel 30 accumulates the signal charges.

Concurrently with the start of the first X-ray irradiation, the source controller 11 sets the irradiation time of the first X-ray irradiation, and turns on the timer 25. When the timer 25 judges that the irradiation time of the first X-ray irradiation has elapsed (Yes in step S14), the source controller 11 stops the first X-ray irradiation (step S15). After stopping the first X-ray irradiation, the source controller 11 transmits the irradiation stop signal to the electronic cassette 13. Upon receiving the irradiation stop signal, the sensor panel 30 finishes the accumulation operation and starts the readout operation of the first image data in the electronic cassette 13 (step S16). The sensor panel 30 outputs the first image data to the memory 54. After finishing the readout operation of the first image data, the sensor panel 30 restarts the reset operation for the preparation of the second accumulation operation.

Unless the full pressing of the irradiation switch 12 is cancelled, the source controller 11 transmits and receives the synchronizing signals for the second X-ray irradiation to and from the electronic cassette 13 as soon as the first X-ray irradiation is finished. At the point of time when the readout operation of the first image data is completed and the preparation for starting the accumulation operation is ready, the electronic cassette 13 transmits the irradiation permission signal to the source controller 11. Upon receiving the irradiation permission signal, the source controller 11 starts the second X-ray irradiation (step S17). Concurrently, the source controller 11 sets the irradiation time of the second X-ray irradiation, and turns on the timer 25. After transmission of the irradiation permission signal, the sensor panel 30 starts the second accumulation operation in the electronic cassette 13 (step S18).

The image processing section 60 subjects the first image data to various types of correction processing in the electronic cassette 13. The preview image producing circuit 65 produces the preview image based on the first image data which has been subjected to the correction processing. Then, the preview image producing circuit 65 transmits the produced preview image to the console 14 during the second accumulation operation (step S19). Since the transmission of the preview image is performed except a period of time during which the second accumulation operation is performed, communication noise is not added to the second image data.

Upon receiving the preview image from the electronic cassette 13, the console 14 displays the preview image on the monitor 14b (step S19). The operator measures success and failure of the X-ray imaging by observing the preview image. In the case where a failure of the X-ray imaging is found, the operator cancels the pressing of the irradiation switch 12, so as to urgently stop the second X-ray irradiation.

When the timer 25 judges that the irradiation time of the second X-ray irradiation has elapsed (Yes in step S20), the source controller 11 stops the second X-ray irradiation (step S21). After stopping the second X-ray irradiation, the source controller 11 transmits the irradiation stop signal to the electronic cassette 13. Upon receiving the irradiation stop signal, the sensor panel 30 finishes the accumulation operation and performs the readout operation for reading out the second image data in the electronic cassette 13 (step S22). The sensor panel 30 outputs the second image data to the memory 54. After finishing the readout operation for reading out the second image data, the sensor panel 30 returns to the standby mode for performing the reset operation from the imaging mode.

The processing section 60 subjects the second image data to the various types of correction processing. Then, the image processing section 60 adds up the first and second image data, each of which has been subjected to the correction processing, in the image addition circuit 66, so as to produce the X-ray image for diagnosis, and stores the produced data of the X-ray image for diagnosis in the memory 54. Thereby, the procedure for performing X-ray imaging once is completed. The electronic cassette 13 transmits the X-ray image for diagnosis stored in the memory 54 to the console 14 through the communication I/F 55. The console 14 displays the X-ray image for diagnosis instead of the preview image on the monitor 14b. The X-ray image for diagnosis, which has been checked by the operator, is transmitted from the console 14 to an image server or the like and used for diagnosis by a doctor.

As described above, in this embodiment, the X-rays are irradiated twice in performing X-ray imaging once. During the second X-ray irradiation, the preview image is produced based on the first image data outputted in the first X-ray irradiation. Before the second X-ray irradiation is finished, the preview image is transmitted to the console 14 and displayed on the monitor 14b. Therefore, the preview image is displayed more promptly in comparison with a conventional technique in which X-rays are irradiated once in performing X-ray imaging once, a preview image is produced based on an X-ray image read out after completion of the X-ray irradiation, and the preview image is transmitted to the console 14 and displayed. Consequently, the waiting time from when the operator presses the irradiation switch to when the preview image is displayed is shortened. Before the second X-ray irradiation is finished, the operator observes the preview image, and can measure success and failure of the X-ray imaging, for example, by checking whether or not the positioning of the object is appropriate. Accordingly, in the case where the positioning of the object or the like is inappropriate, it is possible to promptly prepare for performing X-ray imaging again, and as a result, it is possible to shorten the time required for X-ray imaging operation containing the confirmation operation to be done by the operator.

In the case where the positioning of the object or the like is inappropriate, upon cancellation of the full pressing of the irradiation switch 12, the second X-ray irradiation also can be stopped. Therefore, it is possible to prevent the object from being subjected to unnecessary radiation exposure.

Further, the first image data obtained by the first X-ray irradiation is not only used to produce the preview image but also added to the second image data obtained by the second X-ray irradiation and reflected in the X-ray image for diagnosis. Therefore, the first X-ray irradiation is not wasted.

In the case where the first and second image data respectively obtained by the first and second X-ray irradiation are added up so as to produce the X-ray image for diagnosis as described above, since there is an interval between the first X-ray irradiation and the second X-ray irradiation, the image quality of the X-ray image for diagnosis may be deteriorated due to the effect of body motion of the object. However, according to this embodiment, after the first X-ray irradiation is finished, as soon as the first image data is read out by the sensor panel 30, the second X-ray irradiation is started. Therefore, the interval between the first X-ray irradiation and the second X-ray irradiation is small, and the effect of body motion of the object is suppressed to be small.

Since the preview image is transmitted from the electronic cassette 13 to the console 14 before the sensor panel 30 performs the readout operation after the second X-ray irradiation, noise caused by transmission of the preview image is not added to the second image data obtained by the second X-ray irradiation, and thus good image quality can be achieved.

The first image data read out from the memory 54 is subjected to the binning processing or the thinning processing in the manner of software to produce the preview image in the above embodiment. However, the preview image may be produced by hardware-oriented approach such as thinning reading instead of all-pixels reading during the readout operation after the first X-ray irradiation is finished. In this case, the accumulation operation is continued in the pixels, which have not been subjected to the thinning reading, during a period of time from the start of the first X-ray irradiation to the end of the second X-ray irradiation, and after the second X-ray irradiation is finished, the second image data is read out and added to the first image data in the image addition circuit 66. Alternatively, the following may be performed. After the first readout operation, the reset operation is performed to discharge the accumulated electric charges from the pixels which have not been subjected to the thinning reading. After the preview image is transmitted to the console 14, the pixel values of the pixels which have not been subjected to the thinning reading are generated by interpolation using the pixel values of the pixels which have been subjected to the thinning reading. Then, the generated pixel values of the pixels which have not been subjected to the thinning reading are added to the first image data, and further added to the second image data.

Second Embodiment

It is to be noted that body motion of an object may be detected based on the first and second image data respectively obtained by the first X-ray irradiation and second X-ray irradiation as described hereinbelow.

Figure 8:
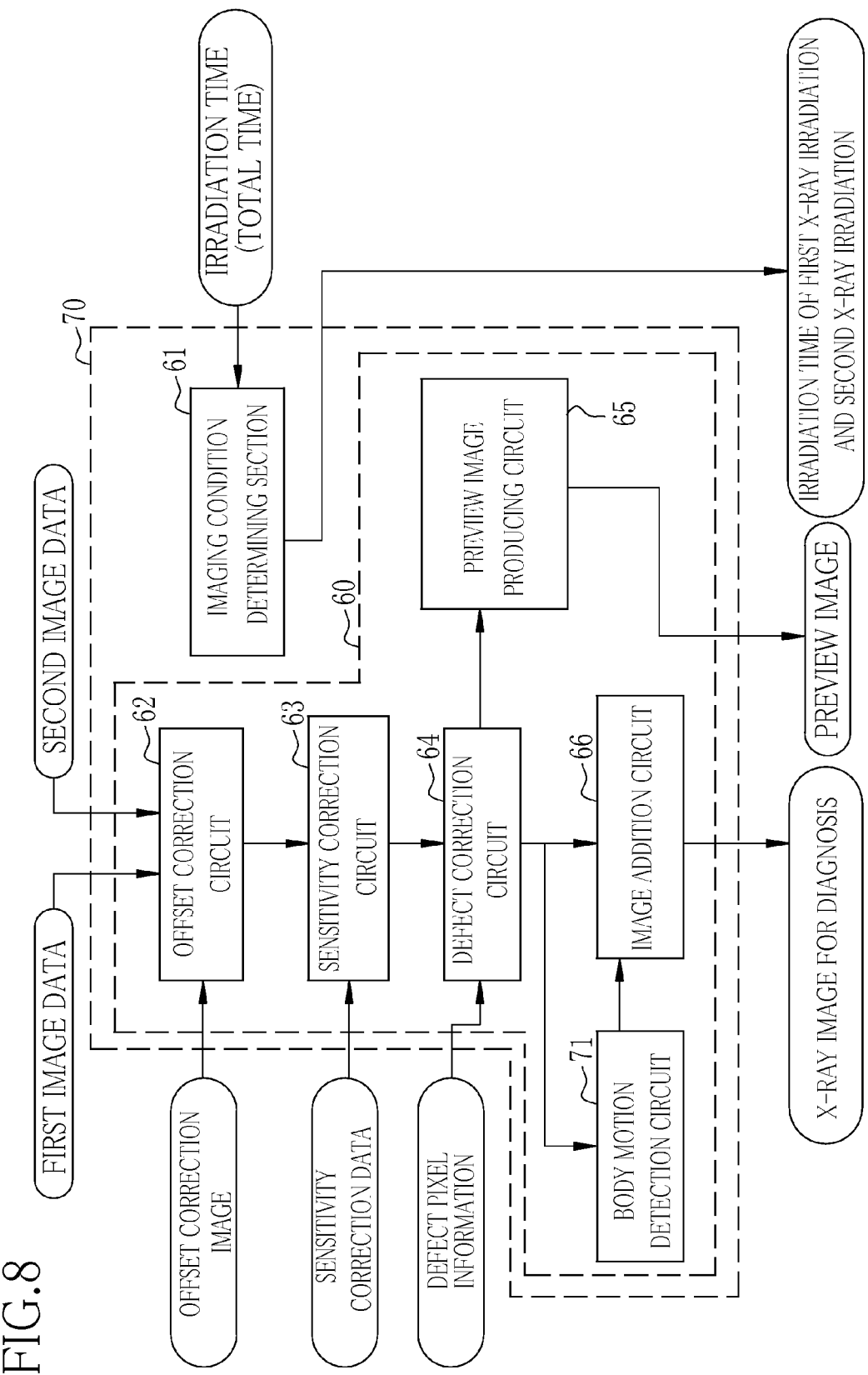
FIG. 8 is a block diagram showing an internal structure of a control unit of an electronic cassette according to a second embodiment.

In FIG. 8, a control unit 70 is provided with a body motion detection circuit 71 (corresponding to a body motion detecting portion). Except the provision of the body motion detection circuit 71, the control unit 70 has the same structure as that of the control unit 48 in the first embodiment. After the second X-ray irradiation is finished, the body motion detection circuit 71 reads out the first image data obtained by the first X-ray irradiation and subjected to the image processing and the second image data obtained by the second X-ray irradiation and subjected to the image processing from the memory 54, and compares them. Then, the body motion detection circuit 71 adopts a well-known motion detection technique using object contour extraction, a motion vector, or the like, so as to quantitatively detect how much the object moves from the position where the object was located in the first X-ray irradiation to the position where the object is located in the second X-ray irradiation.

In the case where the body motion amount of the object detected by the body motion detection circuit 71 is equal to or less than a predetermined threshold value, the image addition circuit 66 adds up the first image data obtained by the first X-ray irradiation and the second image data obtained by the second X-ray irradiation. In the case where the body motion amount of the object is more than the threshold value, the image addition circuit 66 does not perform the addition operation. Thereby, it is possible to prevent deterioration of the image quality of the X-ray image for diagnosis due to the effect of body motion of the object during each of the first X-ray irradiation and the second X-ray irradiation. Additionally, it is possible to prevent a situation that a diagnosis is made based on an X-ray image having an image quality inappropriate for diagnosis.

Figure 9:
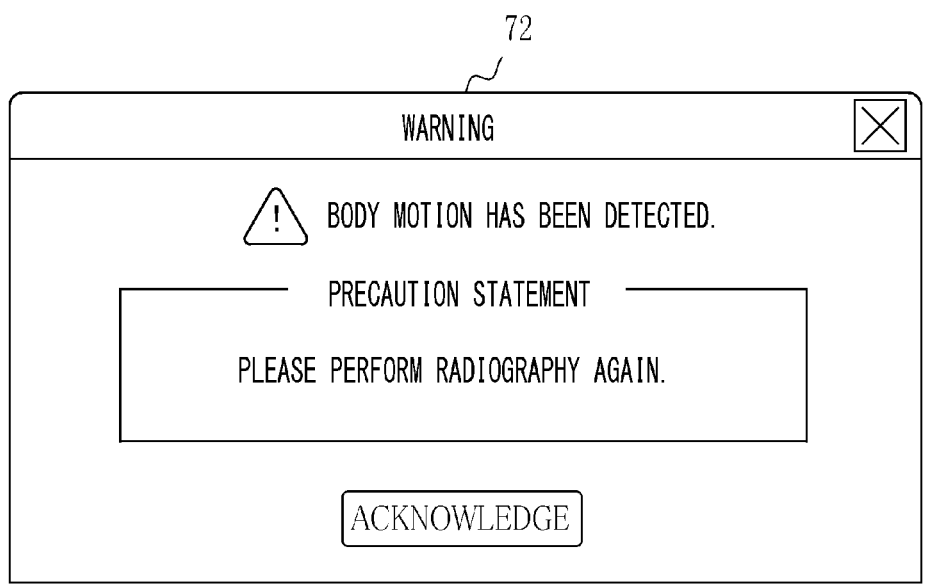
FIG. 9 is a view showing a warning window displayed on a monitor of the console in the case where a body motion detection circuit detects body motion of an object.

Note that, in the case where the body motion amount of the object detected by the body motion detection circuit 71 is more than the threshold value, a message for indicating that body motion of the object has been detected during the first X-ray irradiation and the second X-ray irradiation, which is exemplified by a warning window 72 in FIG. 9, may be displayed on the monitor 14b of the console 14, instead of transmitting the X-ray image for diagnosis to the console 14, so as to prompt the operator to perform X-ray imaging again. Alternatively, the second image data to which the first image data is not added may be transmitted as the X-ray image for diagnosis to the console 14. In the case of displaying the X-ray image on the monitor 14b, it is also possible to notify the operator of information that the first image data has not been added.

The method for displaying the warning in the case where body motion of the object has been detected is not limited to the above-described method in which the warning window 72 is displayed on the monitor 14b. For example, a warning beep sound or the like may be emitted from the electronic cassette 13.

Third Embodiment

Although the first image data is used to produce the preview image in the first embodiment, it is preferable that automatic exposure control (AEC) is performed with use of the first image data in order to improve the image quality of the X-ray image for diagnosis. As described in the first embodiment, although an approximate dose necessary for each part to be imaged is recognized, X-ray transmittance is varied depending on the body frame of the object such as thickness thereof. Therefore, even if the X-rays at the same dose are irradiated from the X-ray source 10, the dose of X-rays reaching the electronic cassette 13 is different for each object. Consequently, the AEC is performed in order to achieve more appropriate image quality. According to the AEC that is commonly performed, an accumulated dose of X-rays reaching the electronic cassette 13 during the X-ray irradiation is monitored, and the X-ray irradiation is stopped when the accumulated dose achieves a target dose. However, according to simplified AEC of this embodiment, by taking advantage of the X-ray irradiation performed twice, based on the first data image obtained by the first X-ray irradiation, the accumulated dose in the first X-ray irradiation is acquired, and based on the acquired accumulated dose in the first X-ray irradiation, the irradiation time of the second X-ray irradiation is determined. Note that, the same components and operations as those in the above embodiments are denoted by the same reference numerals respectively, and the explanation thereof will be omitted.

According to this embodiment, as shown in FIG. 10, irradiation times t1', t2', . . . of the first X-ray irradiation are stored as the item of imaging condition in the storage device 14c of the console 14, instead of the irradiation times t1, t2, . . . for performing X-ray imaging once obtained by adding up the irradiation time of the first X-ray irradiation and the irradiation time of the second X-ray irradiation. Further, information regarding a dose measurement field and a necessary dose is added as the items of the imaging condition.

The dose measurement field represents a field to be referred to at the time of determining the irradiation time of the second X-ray irradiation by the imaging condition determining section 61, and corresponds to a region of interest which is the most remarkable in diagnosis for each part to be imaged. Additionally, a voltage signal can be stably obtained from the dose measurement field. For example, in the case where the body part to be imaged is a chest portion, lung fields are set as the dose measurement field. The dose measurement field is represented by X-Y coordinate. In the case where the dose measurement field is rectangular as in this embodiment, for example, the X-Y coordinates of two points connected by a diagonal line are stored. The X-Y coordinate corresponds to the position of each of the pixels 41 in the imaging area 40 in the electronic cassette 13. An X axis extends in a direction parallel to the scan lines 44, and a Y axis extends in a direction parallel to the signal lines 45. The coordinate of the upper left pixel 41 are assigned as an origin point (0, 0).

In the case where noise, which is added to the voltage signal outputted in the first X-ray irradiation, results in a low S/N ratio, the reliability of the imaging condition for the second X-ray irradiation, which is determined based on the low S/N ratio, is decreased. In order to secure the reliability, the dose in the first X-ray irradiation is preferably set high. However, in principle, since the main X-ray irradiation is the second X-ray irradiation, the dose of the first X-ray irradiation is required to be as low as possible. Therefore, the irradiation time of the first X-ray irradiation is set to a minimum value as long as the imaging condition for the second X-ray irradiation can be reliably determined without being affected by various types of noise added to the voltage signal. The necessary dose is set such that the X-ray image for diagnosis has a preferable image quality for diagnosis.

Figure 11:
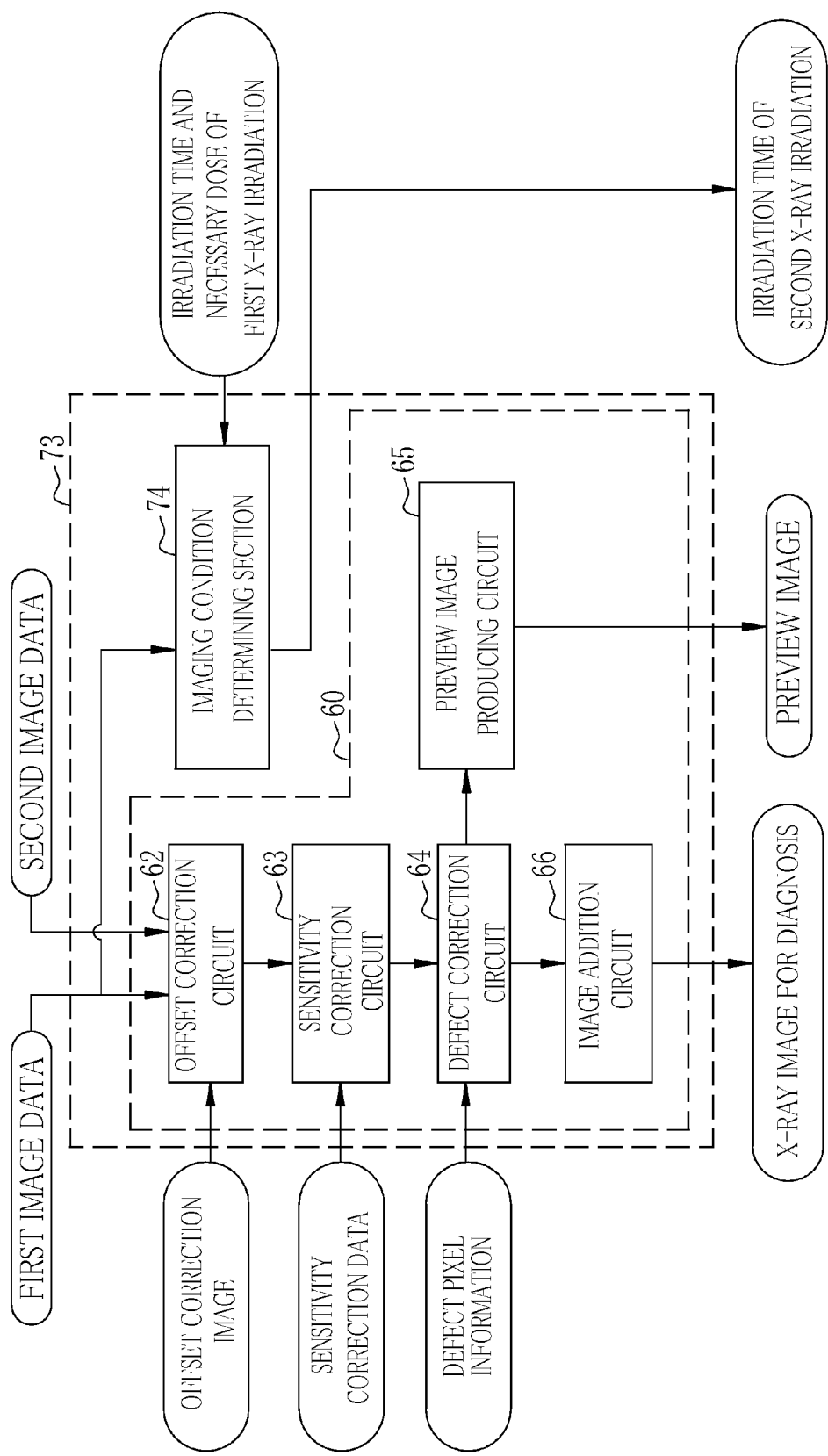
FIG. 11 is a block diagram showing an internal structure of a control unit of an electronic cassette according to a third embodiment.
Figure 12:
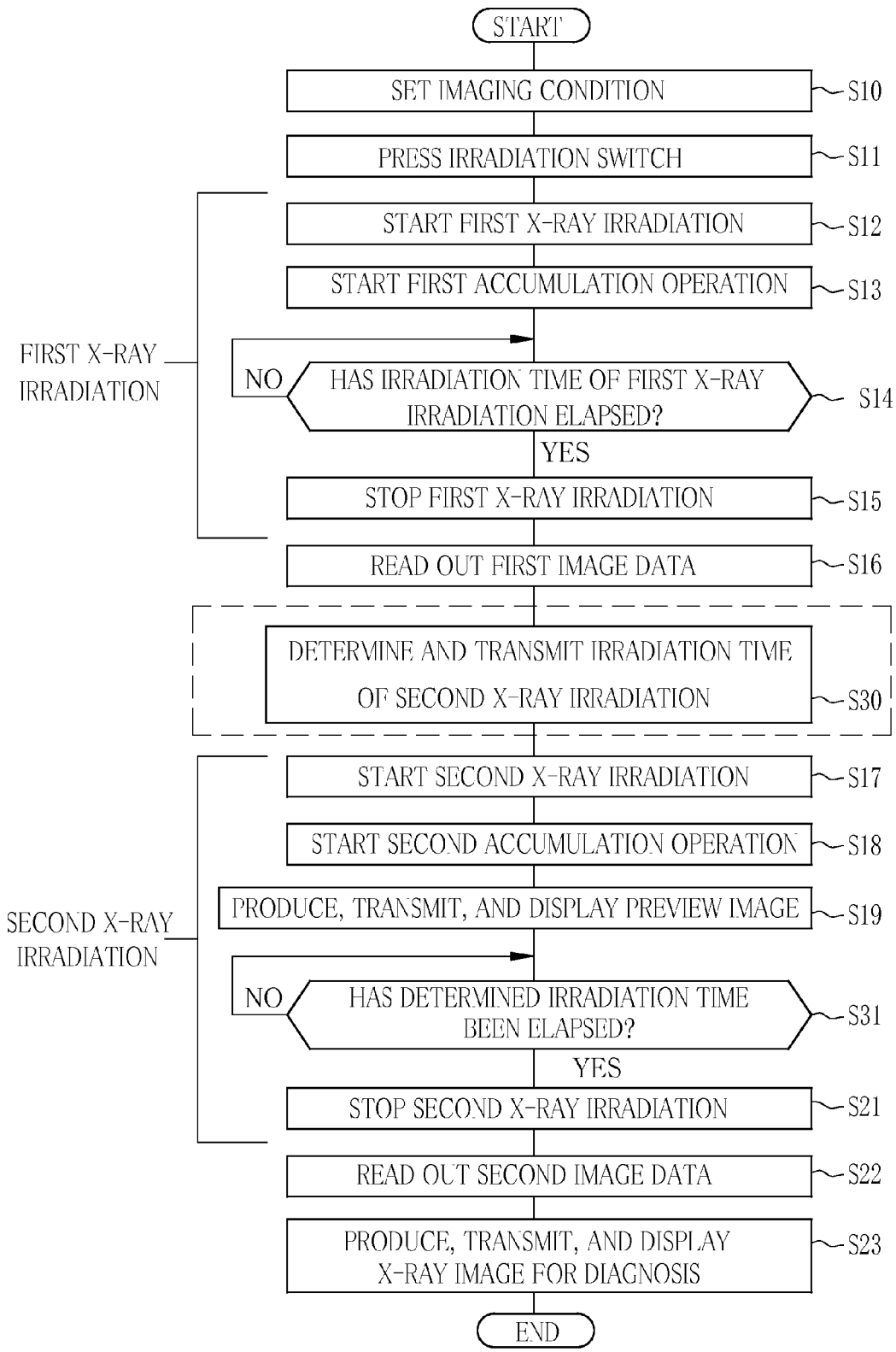
FIG. 12 is a flowchart showing a procedure for X-ray imaging according to a third embodiment.

As shown in FIGS. 11 and 12, after reading out the first image data, an imaging condition determining section 74 of a control unit 73 determines an irradiation time of the second X-ray irradiation based on the irradiation time and the necessary dose of the first X-ray irradiation contained in the imaging condition provided from the electronic cassette 13 and the pixel values of a plurality of the pixels in the dose measurement field contained in the first image data outputted from the sensor panel 30 in the first X-ray irradiation (step S30). Here, the pixel values of a plurality of the pixels in the dose measurement field are identical to the accumulated dose of the X-rays reaching the dose measurement field in the first X-ray irradiation. The imaging condition determining section 74 calculates an average value (a maximum value, a mode value, or a total value is also available) of the pixel values of a plurality of the pixels in the dose measurement field, and divides the calculated average value by the irradiation time of the first X-ray irradiation, so as to obtain a dose per unit time in the first X-ray irradiation. Since the X-rays at a dose corresponding to the average value has been already irradiated in the first X-ray irradiation, the average value is subtracted from the necessary dose. Then, the value resulting from the subtraction is divided by the dose per unit time obtained as described above. Thereby, the irradiation time of the second X-ray irradiation is obtained.

The imaging condition determining section 74 transmits the information regarding the irradiation time of the second X-ray irradiation obtained as described above to the console 14 through the communication I/F 55. The console 14 transmits the received information regarding the irradiation time of the second X-ray irradiation to the source controller 11. The source controller 11 sets the received irradiation time of the second X-ray irradiation to the memory 23. Then, as in the case of the first embodiment, transmission and reception of the synchronizing signals are performed between the source controller 11 and the electronic cassette 13, and the source controller 11 starts the second X-ray irradiation (step S17). Concurrently with this, the source controller 11 sets the irradiation time of the second X-ray irradiation and turns on the timer 25. When the timer 25 judges that the irradiation time of the second X-ray irradiation has elapsed (Yes in step S31), the source controller 11 stops the second X-ray irradiation (step S21).

As an item of the imaging condition for the second X-ray irradiation, a tube current-time product may be determined instead of the irradiation time. In this case, in a similar manner as when the irradiation time is determined, an average value of the pixel values of a plurality of the pixels in the dose measurement field is divided by the tube current-time product of the first X-ray irradiation, so as to obtain a dose per unit tube current-time product in the first X-ray irradiation. Then, the average value is subtracted from the necessary dose, and the value resulting from the subtraction is divided by the dose per unit tube current-time product. Thereby, the tube current-time product of the second X-ray irradiation is obtained. The information regarding the tube current-time product of the second X-ray irradiation is transmitted to the source controller 11.

Fourth Embodiment

According to a fourth embodiment, unlike the third embodiment, AEC is performed in a common manner. Specifically, the first X-ray irradiation is performed without preliminarily determining the irradiation time thereof, the dose of X-rays reaching the electronic cassette 13 during the first X-ray irradiation is monitored, and the X-ray irradiation is stopped when the accumulated dose achieves a target dose. According to the fourth embodiment, the irradiation time from when the first X-ray irradiation is started to when the accumulated dose achieves the target dose is measured, and based on the measured irradiation time, the irradiation time of the second X-ray irradiation is determined. Note that, the same components and operations as those in the above embodiments are denoted by the same reference numerals respectively, and the explanation thereof will be omitted.

According to this embodiment, instead of the irradiation times t1' and t2' of the first X-ray irradiation shown in FIG. 10, an irradiation stop threshold value for determining whether or not to stop the X-ray irradiation during the first X-ray irradiation is stored as the item of the imaging condition in the storage device 14c of the console 14. Further, in the first X-ray irradiation, the irradiation stop signal is transmitted from the electronic cassette 13 to the source controller 11. In response to the reception of the irradiation stop signal by the source controller 11, the first X-ray irradiation is stopped.

Figure 13:
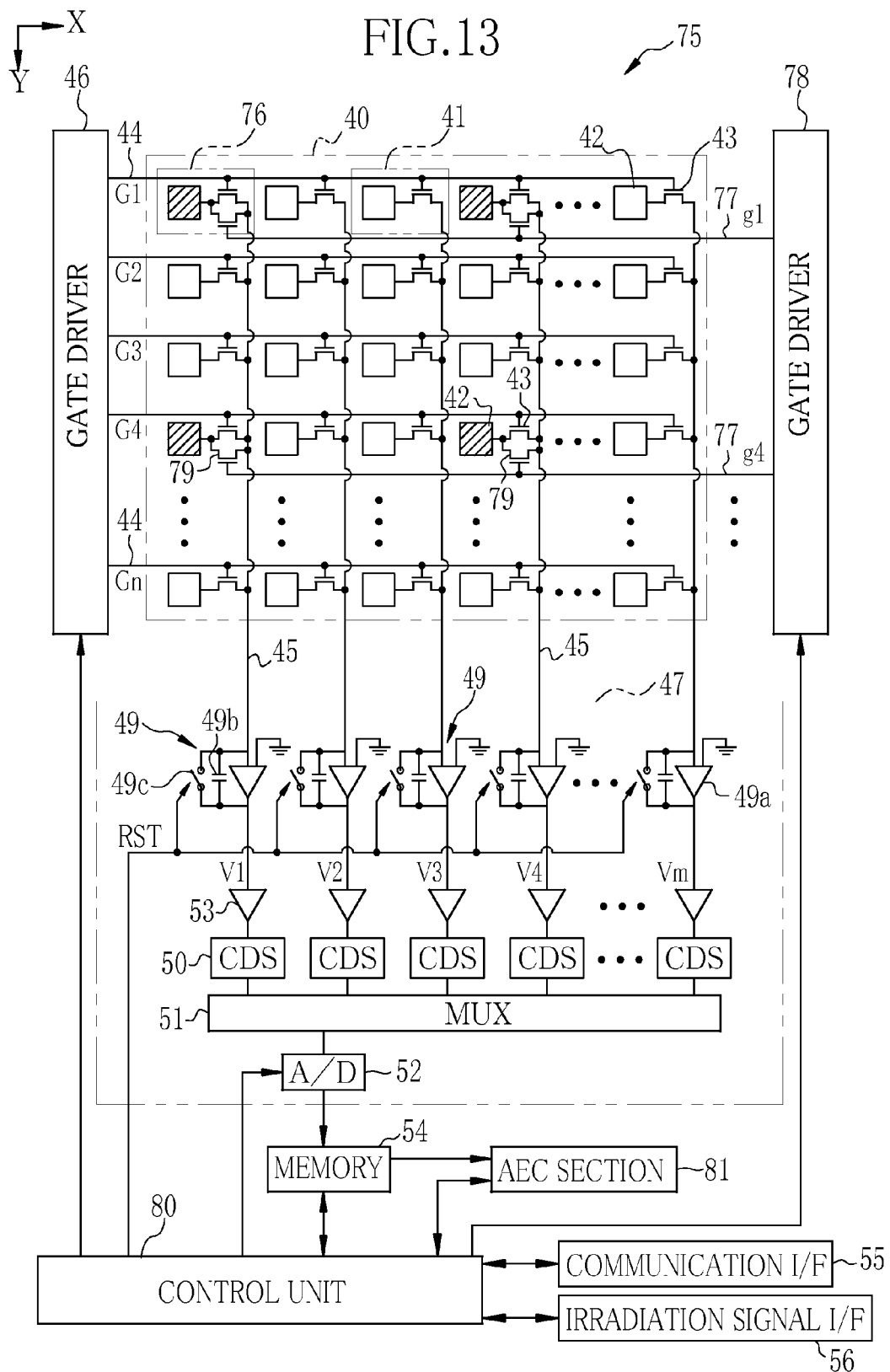
FIG. 13 is a block diagram showing an internal structure of an electronic cassette provided with detection pixels according to a fourth embodiment.

In FIG. 13, a sensor panel 75 includes detection pixels 76. The pixels 41 are used to produce the X-ray image in the conventional manner as in the case of the first embodiment. Each of the detection pixels 76, on the other hand, functions as a dose detection sensor for detecting the X-ray dose received by the imaging area 40, and is used for AEC. Note that, in the drawing, the detection pixels 76 are hatched so as to be distinguished from the pixels 41.

The basic structure including the photoelectric converter 42 and the like is exactly the same between the pixel 41 and the detection pixel 76. Thus, the pixel 41 and the detection pixel 76 can be formed by almost the same manufacturing process. Each of the detection pixels 76 is connected to a TFT 79 driven by a scanning line 77 and a gate driver 78, while the scanning line 77 and the gate driver 78 are respectively different from the scanning line 44 and the gate driver 46 for driving the TFT 43 of the pixel 41. The detection pixel 76 is provided one-by-one for nine pixels arranged in three rows and three columns. Since each of the detection pixels 76 is connected to the TFT 79, the electric charges can be read out from each of the detection pixels 76 even if the TFTs 43 of the pixels 41 in the same row are turned off and the charge accumulation operation is performed.

It is preferable that the ratio of the detection pixels 76 with respect to all the pixels is approximately 0.01%. The positions of the detection pixels 76 have been already known at the time of manufacturing the sensor panel 75, and the sensor panel 75 has a nonvolatile memory (not shown in the drawing) for storing the position (coordinate) of every detection pixel 76 in advance. Note that, in contrast to this embodiment, the detection pixels 76 may be centralized in a particular portion, and the arrangement of the detection pixels 76 may be arbitrarily changed. For example, in a mammography device for breast radiography, the detection pixels 76 are preferably concentrated on a chest wall side.

In the dose detection operation performed during the first X-ray irradiation (i.e. during the accumulation operation of the pixels 41), under the control of the control unit 80, the gate driver 78 transmits the irradiation permission signal to the source controller 11. Upon the shift of the sensor panel 75 from the standby mode for repeating the reset operation to the imaging mode for starting the accumulation operation, the gate driver 78 sequentially issues gate pulses g1, g4, g7, . . . , and gk (k=1+3 (n−1)) each for driving the TFTs 79 in the same row at a time at predetermined intervals, such that the scan lines 77 are sequentially activated on a row-by-row basis. Thus, the TFTs 79 connected to the scan lines 77 are turned on sequentially on a row-by-row basis, and this operation is repeated several times at a predetermined sampling rate. Alternatively, the TFTs 79 of the detection pixels 76 that are present within the dose measurement field are selectively turned on. The electric charges generated in the photoelectric converter 42 of each of the detection pixels 76 flow into the capacitor 49b of the integration amplifier 49 through the signal line 45, upon turning on of the TET 79, irrespective of whether the TFT 43 is turned on or turned off. During the accumulation operation of the pixels 41, the electric charges which are outputted from the detection pixels 76 and accumulated in the integration amplifiers 49 are transmitted to the A/D 52, and converted into a digital voltage signal (hereinafter referred to as a dose signal) by the A/D 52. The dose signal outputted from each of the detection pixels 76 is stored in the memory 54 in association with the coordinate information of each of the detection pixels 76 in the imaging area 40.

As in the case of the control unit 48 of the first embodiment, the control unit 80 controls operation of the sensor panel 75. The control unit 80 makes the sensor panel 75 continue the accumulation operation for accumulating the electric charges in the pixels 41 during a period of time from the start of the first X-ray irradiation to the end of the second X-ray irradiation. Additionally, during the first X-ray irradiation, the control unit 80 makes each of the detection pixels 76 perform the dose detection operation. After the second X-ray irradiation is finished, the control unit 80 makes the sensor panel 75 shift from the accumulation operation to the readout operation. Therefore, the sensor panel 75 outputs the X-ray image data only once each time X-ray imaging is performed. Note that, an operation program is not shown in the drawing.

The operation of an AEC section 81 is controlled by the control unit 80. The AEC section 81 reads out the dose signals obtained at a predetermined sampling rate more than once from the memory 54 during the accumulation operation of the pixels 41, and performs the AEC based on the dose signals thus read out.

The AEC section 81 sequentially adds up the dose signals read out from the memory 54 by the dose detection operation performed more than once for each of the coordinates, so as to measure the accumulated dose of X-rays reaching the imaging area 40. More specifically, based on the information regarding the dose measurement field from the console 14, the AEC section 81 selects the detection pixel 76, from which the dose signal to be used for determining whether or not the accumulated dose of the X-rays has reached the target dose is obtained, out of a plurality of the detection pixels 76 distributed in the imaging area 40. Then, the AEC section 81 calculates an integrated value of the dose signals from each of the selected detection pixels 76 within the dose measurement field. Thereafter, the AEC section 81 obtains an average value (an accumulated dose in the dose measurement field) by adding up the integrated values of the dose signals from the detection pixels 76 and dividing the resultant value by the number of the detection pixels 76. The AEC section 81 compares the obtained average value with the irradiation stop threshold value (target dose) provided by the console 14 at an appropriate timing. When it is determined that the average value exceeds the irradiation stop threshold value and the accumulated dose of X-rays has reached the target dose, the AEC section 81 issues the irradiation stop signal. Note that, in the case where the output of the detection pixels 76 is low obviously due to an implant embedded in the object, the AEC section 81 may judge the situation as abnormal and output the irradiation stop signal so as to interrupt the X-ray irradiation.

In the first X-ray irradiation, the AEC is performed and the irradiation time is measured until the accumulated dose of X-rays achieves the target dose, and therefore the irradiation time of the first X-ray irradiation set in the source controller 11 has a margin in order to prevent X-ray irradiation from being stopped during the measurement of the irradiation time. The irradiation time of the first X-ray irradiation is set by taking into consideration that the irradiation time of the first X-ray irradiation is extremely shorter than that of the second X-ray irradiation and that the irradiation time until the accumulated dose achieves the target dose varies depending on the tube current and the body part to be imaged. The maximum value of the irradiation time set in accordance with safety regulations in the X-ray source 10 also may be used.

In the first X-ray irradiation, the source controller 11 starts the X-ray irradiation in a state that the irradiation time is set. When it is determined by the AEC section 81 that the accumulated dose of the X-rays has achieved the target dose and the source controller 11 receives the irradiation stop signal from the irradiation signal I/F 56 through the irradiation signal I/F 26, the source controller 11 functions to stop the X-ray irradiation even before the irradiation time preliminarily set in the source controller 11 is not achieved. Note that, in the case where the maximum value for the irradiation time is set in the source controller 11, the irradiation time is preferably set in accordance with the body part to be imaged.

Since the dose necessary for the first X-ray irradiation is extremely smaller than that for the second X-ray irradiation, the irradiation time set in the source controller 11 is a value with a margin. However, in fact, the X-ray irradiation is not continued until the irradiation time achieves the set value, and the AEC section 81 stops the X-ray irradiation before the irradiation time achieves the set value. Under the condition that the X-rays at the same tube voltage and tube current are irradiated, in the case where the object is relatively thick, the dose of X-rays having passed through the object and reaching the imaging area 40 per unit time is small, and therefore the irradiation time until the necessary dose for the first X-ray irradiation is achieved becomes long, and in the case where the object is relatively thin, in contrast, the irradiation time until the necessary dose for the first X-ray irradiation is achieved becomes short. Additionally, in the case where the density of the internal body tissue is relatively high, the X-ray transmittance is lowered and the irradiation time becomes long, and in the case where the density of the body tissue is relatively low, in contrast, the irradiation time becomes short. However, in any cases, although the irradiation time is different, the AEC section 81 performs exposure control such that the accumulated dose becomes equal to the dose necessary for the first X-ray irradiation.

Figure 14:
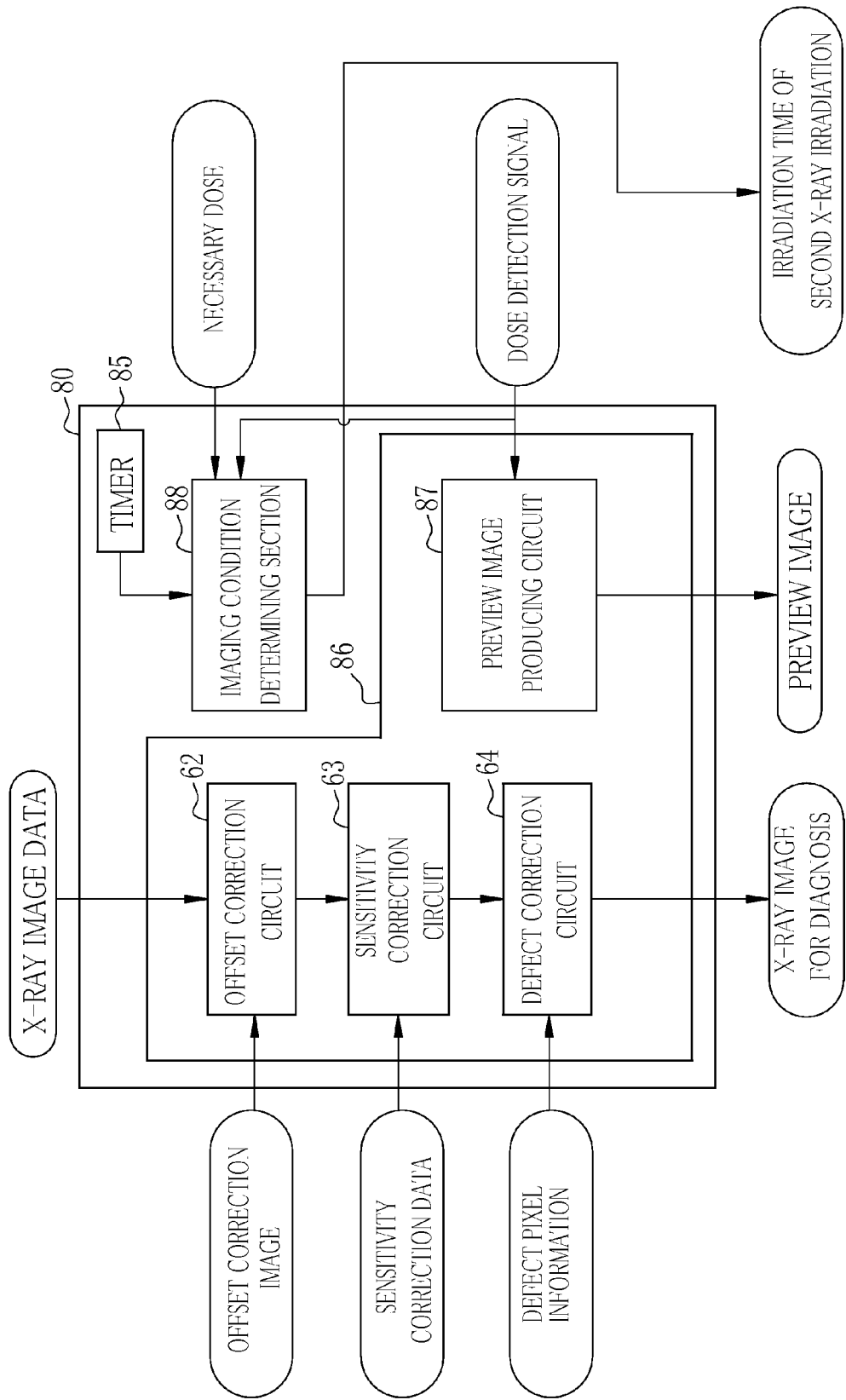
FIG. 14 a block diagram showing an internal structure of a control unit of an electronic cassette according to a fourth embodiment.

In FIG. 14, the control unit 80 has a timer 85. The timer 85 counts the time from when the irradiation permission signal is transmitted to when the irradiation stop signal is transmitted through the irradiation signal I/F 56 in the first X-ray irradiation, namely, the irradiation time of the first X-ray irradiation. The counting result of the timer 85 is transmitted to an imaging condition determining section 88. Further, the necessary dose and the integrated value of the dose signals at the time of transmitting the irradiation stop signal, which are items included in the imaging condition provided by the electronic cassette 13, are also transmitted to the imaging condition determining section 88. Note that, the irradiation time of the first X-ray irradiation may be counted by the source controller 11 and transmitted through the console 14 to the electronic cassette 13.

Here, the integrated value of the dose signals from the detection pixels 76 in the dose measurement field at the time of transmitting the irradiation stop signal represents the accumulated dose of the X-rays having reached the dose measurement field in the first X-ray irradiation, as with the pixel values of a plurality of the pixels in the dose measurement field in the third embodiment. The imaging condition determining section 88 calculates the irradiation time of the second X-ray irradiation with use of the integrated value of the dose signals at the time of transmitting the irradiation stop signal, instead of the average value of the pixel values of a plurality of the pixels in the dose measurement field. Note that, in the similar manner as the third embodiment, the tube current-time product may be determined as the item of the imaging condition for the second X-ray irradiation instead of the irradiation time.

The sensor panel 75 is caused to perform the accumulation operation during the period of time between the start of the first X-ray irradiation and the end of the second X-ray irradiation, and further caused to perform the readout operation after the completion of the second X-ray irradiation. Therefore, an image processing section 86 does not include the image addition circuit 66. The electric charges generated in the first X-ray irradiation is added to the electric charges generated in the second X-ray irradiation in each of the pixels 41. The X-ray image data read out in the readout operation after the completion of the second X-ray irradiation is subjected to various types of image processing and transmitted as the X-ray image for diagnosis to the console 14.

Figure 15:
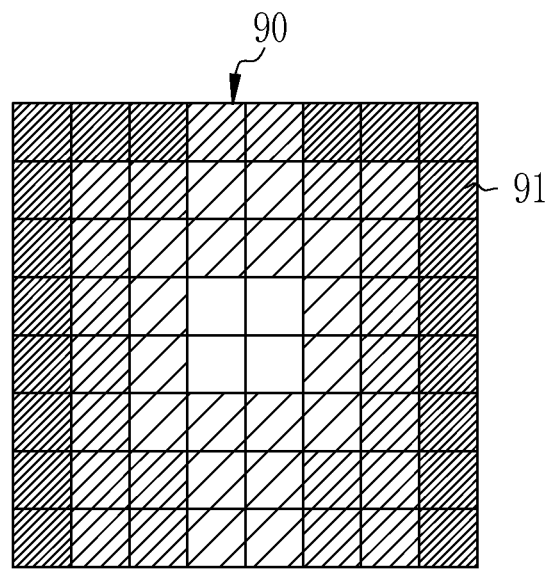
FIG. 15 is a view showing a preview image.

A preview image producing circuit 87 produces a preview image 90 as shown in FIG. 15 based on the dose signals outputted from the detection pixels 76 by the dose detection operation in the first X-ray irradiation.

In FIG. 15, the preview image 90 represents the amount of the X-ray dose received by the imaging area 40 on the basis of each of divided portions 91 into which the imaging area 40 is equally divided. Each of the divided portions 91 includes a plurality of the pixels 41 and at least one detection pixel 76. According to this embodiment, for example, 9 pieces of pixels arranged in three rows and three columns, in which one detection pixel 76 is included, constitutes one divided portion 91. The preview image producing circuit 87 calculates an average value (a maximum value, a mode value, or a total value is also available) of the dose signals from the detection pixels 76 contained in each of the divided portions 91. Further, the preview image producing circuit 87 integrates the average value of the dose signal of each of the divided portions 91 obtained by sampling performed more than once. The preview image producing circuit 87 produces the preview image 90 by regarding the divided portions 91 as pixels, and regarding the integrated value of the dose signal of each of the divided portions 91 as a pixel value.

The narrow-hatched divided portions 91 corresponding to non-detection portions, to which the X-rays are directly applied without passing through the object, have large integrated values. The non-hatched divided portions 91, to which the X-rays are applied after passing through a relatively thick body part of the object, have small integrated values. The wide-hatched divided portions 91 corresponding to a boundary between the non-detection portion and the object or corresponding to a portion to which the X-rays are applied after passing through a relatively thin body part of the object have the middle integrated values.

The resolution of the preview image 90 is increased with the increase in the number of the divided portions 91, however the resolution comparable to the resolution of the X-ray image for diagnosis is not necessary, as long as the positioning of the object can be confirmed. The preview image 90 may be produced based on the integrated value of the dose detection signals obtained by a specific number-th sampling (for example, first sampling) or the integrated value of the dose detection signals obtained by a first few samplings, instead of the integrated value of the dose detection signals obtained by the samplings performed plural times during the period of time between the start and end of the first X-ray irradiation. Accordingly, it is possible to produce the preview image 90 before the first X-ray irradiation is finished, and it becomes possible to display the preview image 90 more promptly.

Next, with reference to a flowchart in FIG. 16, an operation of this embodiment is explained. Note that, the same steps as those in the above embodiments are denoted by the same reference numerals respectively, and the explanation thereof will be omitted.

At first, transmission/reception of the irradiation start request signal and the irradiation permission signal is performed between the source controller 11 and the electronic cassette 13. Then, the sensor panel 30 finishes the reset operation, starts the accumulation operation and the dose detection operation (step S35), and shifts from the standby mode to the imaging mode. Concurrently with this, the timer 85 starts counting the irradiation time of the first X-ray irradiation.

In the dose detection operation, the dose signal corresponding to the electric charges generated in the detection pixels 76 is read out at a predetermined sampling rate more than once, and transmitted to the AEC section 81. Based on the information of the dose measurement field provided by the console 14, the AEC section 81 integrates the dose signals of the detection pixels 76 which exist in the dose measurement field out of the dose signals of a plurality of the detection pixels 76 (step S36). Then, the AEC section 81 compares the integrated value with the irradiation stop threshold value (step S37).

When the integrated value achieves the irradiation stop threshold value (Yes in step S38), the AEC section 81 judges that the accumulated dose of the X-rays has achieved the target dose, and outputs the irradiation stop signal. The irradiation stop signal is transmitted from the irradiation signal I/F 56 to the irradiation signal I/F 26. Concurrently with this, the timer 85 stops counting the irradiation time of the first X-ray irradiation. Upon receiving the irradiation stop signal, the source controller 11 stops the first X-ray irradiation from the X-ray source (step S15). The sensor panel 75 continues the accumulation operation.

After the transmission of the irradiation stop signal, the counting result of the irradiation time of the first X-ray irradiation by the timer 85 and the integrated value of the dose signals at the time of transmitting the irradiation stop signal are transmitted to the imaging condition determining section 88. The imaging condition determining section 88 determines the irradiation time of the second X-ray irradiation based on the necessary dose received from the console 14, the irradiation time of the first X-ray irradiation received from the timer 85, and the integrated value of the dose signals at the time of transmitting the irradiation stop signal from the AEC section 81. The information of determined irradiation time is transmitted through the communication I/F 55 to the console 14, and further transmitted from the console 14 to the source controller 11 (step S39).

During the second X-ray irradiation (i.e. during the accumulation operation by the sensor panel 30), the preview image producing circuit 87 produces the preview image 90 based on the dose signals outputted from the detection pixels 76 in the dose detection operation during the first X-ray irradiation. The preview image 90 is transmitted through the communication I/F 55 to the console 14, and displayed on the monitor 14b of the console 14 (step S19).

The first X-ray irradiation is continued until the accumulated dose achieves the dose necessary for determining the imaging condition for the second X-ray irradiation. The irradiation time as the item of the imaging condition for the second X-ray irradiation is determined based on the integrated value of the dose signals detected by the detection pixels 76 in the first X-ray irradiation, the irradiation time of the first X-ray irradiation counted by the timer 85, and the necessary dose. Therefore, the second X-ray irradiation can be always performed under the appropriate imaging condition, irrespective of individual difference in body frame of the object, the density of the internal body tissue, and the like.

It is to be noted that the second embodiment and the fourth embodiment may be combined. For example, the dose detection operation is performed not only in the first X-ray irradiation but also in the second X-ray irradiation, and based on the dose signals outputted from the detection pixels 76 by the dose detection operation, an image for body motion detection is produced in the preview image producing circuit 87 by the same method as that for producing the preview image. Then, the body motion of the object may be detected by the body motion detection circuit 71 with use of the preview image and the image for body motion detection which are produced based on the dose signals outputted from the detection pixels 76 by the dose detection operation in the first and second X-ray irradiation.

The body motion detection circuit 71 may detect the body motion of the object during the second X-ray irradiation instead of after the second X-ray irradiation. In this case, the preview image producing circuit 87 produces the image for body motion detection whenever one to several dose detection signals are sampled by the dose detection operation in the second X-ray irradiation. The body motion detection circuit 71 compares the image for body motion detection transmitted from the preview image producing circuit 87 whenever one to several dose detection signals are sampled during the second X-ray irradiation with the preview image produced during the first X-ray irradiation, so as to detect the presence or absence of the body motion of the object in the similar manner as mentioned above. If the presence of body motion of the object is detected, the body motion detection circuit 71 transmits the irradiation stop signal through the irradiation signal I/F 56 to the source controller 11.

Upon receiving the irradiation stop signal through the irradiation signal I/F 26 from the body motion detection circuit 71, the source controller 11 stops the X-ray irradiation as with the case where the irradiation stop signal is received from the AEC section 81 in the fourth embodiment. The presence or absence of the body motion of the object is detected in real time during the second X-ray irradiation, and the X-ray irradiation is stopped during the second X-ray irradiation in the case where the presence of the body motion is detected. Thus, it is possible to prevent unnecessary radiation exposure to the object. Note that, in the case where presence of the body motion of the object is detected, the warning window 72 shown in FIG. 9 may be displayed so as to give warning.

In the case where the body motion detection circuit 71 detects the body motion of the object, the X-ray image may not be outputted to the console 14 by preventing the sensor panel from performing the readout operation or by erasing the data from the memory 54 after the readout operation. However, in the case where the second X-ray irradiation is stopped in response to detection of the body motion of the object by the body motion detection circuit 71 and the actual irradiation time is close to the irradiation time determined by the imaging condition determining section 88, the obtained X-ray image possibly has the image quality comparable to the image quality of the X-ray image obtained by performing the second X-ray irradiation for the irradiation time determined by the imaging condition determining section 88 in a state that the presence of body motion of the object is not detected. Further, since the X-ray irradiation is stopped upon the detection of the body motion of the object by the body motion detection circuit 71, the body motion possibly has little effect on the X-ray image. For this reason, even if the body motion detection circuit 71 detects the body motion of the object, the sensor panel preferably performs the readout operation and outputs the X-ray image at any rate. The operator may judge whether or not the X-ray image has the image quality adequate for diagnosis.

The images for body detection may be compared with each other, instead of comparing the image for body detection with the preview image, so as to detect the body motion of the object.

Although the detection pixel 76 provided with the TFT 79 driven separately from the TFT 43 is exemplified, the detection pixel may be a pixel 101 in which the TFT 43 has a short between the source electrode and the drain electrode or a pixel 102 in which the TFT 43 is not provided and the photoelectric converter 42 is directly connected to the signal line 45 in a sensor panel 100 shown in FIG. 17.

In this case, the electric charges generated in the photoelectric converter 42 of the detection pixel 101 or 102 are accumulated in the capacitor 49b of the integration amplifier 49 irrespective of whether the TFT 43 is turned on or turned off. Therefore, the electric charges are not accumulated in the photoelectric converters 42, and the dose signal can be obtained by reading out the voltage signal corresponding to the electric charges from the integration amplifiers 49. Consequently, the speed of outputting the dose signal is accelerated in comparison with the sensor panel 75 shown in FIG. 13 in which the TFTs 79 are turned on to read out the dose signals. In the case where the imaging condition for the second X-ray irradiation is determined based on the result of the first X-ray irradiation in which the AEC is performed, the dose signal is promptly outputted, and therefore it is possible to finish the AEC processing quickly. As a result of this, the determination of the imaging condition for the second X-ray irradiation can be accelerated. Namely, it is the most appropriate to determine the imaging condition for the second X-ray irradiation based on the result of the first X-ray irradiation in which the AEC is performed.

Note that, since the detection pixels 101 or 102 are regarded as defect pixels in some cases, the detection pixels 101 or 102 are partially arranged, and the number of the detection pixels 101 or 102 is small with respect to the total number of the pixels 41. In the case where the output of such a detection pixel 101 or 102 is used to perform the AEC and such a detection pixel 101 or 102 is regarded as the defect pixel, it is considered that the image data is thinned by the amount corresponding to the detection pixels 101 or 102. Consequently, in the case where the AEC is performed in the manner described above, it is effective that the dose signals from the detection pixels 101 or 102 to be used to perform the AEC are reused to produce the preview image 90. Additionally, it is possible to avoid the trouble of having to perform the readout operation of the first image data after the first X-ray irradiation to produce the preview image as performed in the first embodiment, and therefore the processing can be accelerated.

In the above embodiments, each of the detection pixels is formed to have approximately the same size as that of one pixel, and the detection pixels are provided instead of some of the pixels, such that some of the pixels are used as the detection pixels. However, the size of each of the detection pixels is arbitrarily changeable, and may have a size smaller than that of one pixel, or may have a size equivalent to plural pixels. Further, the detection pixel may be provided between the pixels adjacent to each other. The shape of the detection pixel is not limited to an approximately square shape, and may be a rectangular shape.

With taking advantage of the fact that electric current flowing through the bias line, which supplies the bias voltage to each of the pixels, corresponds to the amount of the electric charges generated in each of the pixels, the value of electric current flowing through the bias line connected to a specific pixel may be monitored to detect the X-ray dose. In this case, the pixel having the electric current value to be monitored is designated as the detection pixel. Similarly, the leak current flowing from the pixel may be monitored to detect the X-ray dose, and also in this case, the pixel having the leak current to be monitored is designated as the detection pixel.

Furthermore, the detection pixel, which can be formed in a manufacturing process similar to that of the normal pixel, is used as a dose detection sensor in the above embodiments. However, a dose detection sensor, whose structure, material, manufacturing process, and the like are different from those of the normal pixel, may be used. However, it is difficult to form the dose detection sensors each having a structure different from that of the normal pixel in the imaging area, because the manufacturing process of the dose detection sensors is different from that of the normal pixels. In order to facilitate the manufacturing process of the dose detection sensors, the detection pixels, which can be formed in the manufacturing process approximately similar to that of the normal pixel as described, are preferably used as the dose detection sensors. Further, the dose detection sensor is not necessarily formed in the imaging area of the sensor panel, and a dose detection sensor formed separately from the sensor panel may be used. However, the provision of the dose detection sensor which is separate from the sensor panel causes an increase in size and manufacturing cost. Accordingly, as described in the above embodiments, the dose detection sensor is preferably the detection pixel formed in the imaging area of the sensor panel.

In the case of using the dose detection sensor having a structure different from that of the normal pixel, it is impossible to produce the preview image from the dose signal unlike the fourth embodiment. However, according to the present invention, it is also possible to use the dose detection sensor for only performing the AEC so as to produce the preview image from the first image data, in combination with the first embodiment.

In the fourth embodiment, it is determined that the accumulated dose has reached the target dose when the integrated value of the dose signals reaches the irradiation stop threshold value, and then the irradiation stop signal is outputted. Alternatively, the time at which the accumulated dose of X-rays reaches the target dose may be predicted based on the integrated value of the dose signals so as to transmit the irradiation stop signal to the source controller at the moment when the predicted time comes, or information of the predicted time itself may be transmitted to the source controller. In the latter case, the source controller measures the irradiation time, and stops the X-ray irradiation at the moment when the irradiation time reaches the predicted time.

Although the preview image is produced based on the data obtained by the first X-ray irradiation (corresponding to the first image data in the first to third embodiments, and the dose signal in the fourth embodiment) in the above embodiments, a second preview image may be produced based on the data of the X-ray image for diagnosis (corresponding to the data obtained by adding up the first and second image data in the image addition circuit 66 in the first to third embodiments, and the X-ray image data read out in the readout operation after the second X-ray irradiation is finished in the fourth embodiment). In this case, as with the first embodiment, the preview image producing circuit subjects the data of the X-ray image for diagnosis to the binning processing or the thinning processing so as to produce the second preview image. After the second X-ray irradiation is finished, the electric cassette transmits the second preview image to the console, and the console displays the received second preview image on the monitor. Thereafter, the electronic cassette transmits the X-ray image for diagnosis which has not been subjected to the binning processing or the thinning processing to the console, and the console displays the X-ray image for diagnosis instead of the second preview image on the monitor. Since the second preview image is displayed on the monitor, it is possible to reconfirm a portion which is unclear in the first preview image.

Although the preview image is displayed on the monitor of the console in the above embodiments, the electronic cassette may include a monitor for displaying the preview image.

Although the console 14 and the electronic cassette 13 are separated from each other in the above embodiments, the console 14 may not be necessarily independent of the electronic cassette 13. The functions of the electronic cassette 13 may be installed into the console 14. For example, the console 14 may have the function of the imaging condition determining section, such that the console 14 determines the imaging condition for the second X-ray irradiation. Further, the control unit 48 having the function of producing the preview image may be provided in the console 14. In the case where the control unit 48 is provided in the electronic cassette 13 as with the above embodiments, the control unit 48 in the electronic cassette 13 functions as the transmitting portion for transmitting the preview image through the communication I/F to the console 14 having the monitor 14b. However, in the case where the control unit 48 is provided in the console 14, the control unit 48 functions as the outputting portion for outputting the preview image to the monitor 14b without the intermediation of the communication I/F 55. Furthermore, the source controller 11 and the console 14 may be integrated together. In contrast, a specific imaging control device having the functions of the imaging condition determining section and the like may be provided between the electronic cassette and the console.

Further, the present invention is applicable to not only an electronic cassette as a portable X-ray image detecting device but also an X-ray image detecting device installed on an imaging table. As a matter of course, the present invention is also applicable to a storage medium in which an operation program for the radiation image detecting device is stored. The storage medium stores the operation program which is readable by a computer such as the control unit 48. By executing the operation program by the computer, it is possible to cause the computer to function as part of the radiation image detecting device. Furthermore, the present invention is applicable not only the case of imaging X-rays but also the case of imaging radiation such as gamma rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

Incidentally, it is possible to identify the invention described in the following additional claims based on the above explanation.

[Additional Claim 1]

A radiation imaging system comprising:
  a radiation source for irradiating radiation to an object;
  a source controller for controlling operation of the radiation source such that radiation is irradiated twice in performing radiography once to acquire one sheet of radiation image for diagnosis of the object;
  a radiation image detecting device including a sensor panel having an imaging area in which pixels for accumulating electric charges corresponding to a dose of radiation having passed through the object are arranged, the radiation image detecting device detecting the radiation image for diagnosis by the sensor panel; and
  a monitor for displaying the radiation image, wherein
  the radiation image detecting device comprising:
    a data obtaining portion for obtaining data for producing a preview image to be displayed on the monitor prior to displaying the radiation image for diagnosis by first radiation irradiation;
    a preview image producing portion for producing the preview image based on the data obtained by the data obtaining portion;

an outputting portion for starting output of the preview image produced by the preview image producing portion to the monitor before second radiation irradiation is finished; and a plurality of dose detection sensors each for detecting a dose of radiation reaching the imaging area in the first radiation irradiation and outputting a dose signal corresponding to the detected dose in order to perform exposure control of the radiation image for diagnosis, each of the dose detection sensors detects a dose more than once at least during the first radiation irradiation, and the radiation image detection device further comprises a second body motion detecting portion for detecting presence or absence of body motion of the object based on a comparison result of the dose signals outputted from the dose detection sensors more than once.

[Additional Claim 2]

The radiation imaging system according to additional Claim 1, wherein the second body motion detecting portion outputs an irradiation stop signal for stopping the first radiation irradiation or the second radiation irradiation to the source controller in the case of detecting body motion of the object.

What is claimed is:

1. An x-ray radiation imaging system comprising:
   an x-ray radiation source for emitting x-ray radiation to an object;
   a source controller for controlling operation of the x-ray radiation source such that x-ray radiation is emitted twice in performing radiography once to acquire one sheet of x-ray radiation image for diagnosis of the object;
   an x-ray radiation image detecting device for detecting the x-ray radiation image for diagnosis based on x-ray radiation having passed through the object; and
   a monitor for displaying the x-ray radiation image,
   wherein
   the x-ray radiation image detecting device comprises:
      a sensor panel having an imaging area in which pixels are arranged, each of the pixels accumulating signal charges that correspond to an x-ray radiation dose and are used for generating the x-ray radiation image for diagnosis;
      a data obtaining portion for obtaining data for producing a preview image based on the signal charges being used for generating the x-ray radiation image for diagnosis by first x-ray radiation emission, the preview image being displayed on the monitor prior to displaying the x-ray radiation image for diagnosis;
      a preview image producing portion for producing the preview image based on the data obtained by the data obtaining portion; and
      an outputting portion for starting output of the preview image produced by the preview image producing portion to the monitor before second x-ray radiation emission is finished.

2. The x-ray radiation imaging system according to claim 1, further comprising an irradiation switch for inputting a command to start radiation emission to the source controller, wherein
   the source controller makes the x-ray radiation source start the first x-ray radiation emission upon receiving the command to start radiation emission from the irradiation switch once, and makes the x-ray radiation source start the second x-ray radiation emission automatically after the first x-ray radiation emission is finished.

3. The x-ray radiation imaging system according to claim 1, wherein the x-ray radiation image detecting device further comprises:
   a control unit for making the sensor panel perform an accumulation operation for accumulating the electric charges in the pixels and a readout operation for reading out the accumulated electric charges from the pixels.

4. The x-ray radiation imaging system according to claim 3, wherein
   the x-ray radiation image detecting device is separate from the monitor,
   the outputting portion is identical to a transmitting portion for transmitting the preview image to the monitor, and
   the transmitting portion completes transmission of the preview image before the sensor panel starts the readout operation after the second x-ray radiation emission is finished.

5. The x-ray radiation imaging system according to claim 4, wherein the transmitting portion transmits the preview image while the sensor panel performs the accumulation operation in the second x-ray radiation emission.

6. The x-ray radiation imaging system according to claim 3, wherein the data obtaining portion obtains data for producing the preview image from the sensor panel.

7. The x-ray radiation imaging system according to claim 6, wherein
   the control unit makes the sensor panel perform the readout operation every time each of the first x-ray radiation emission and the second x-ray radiation emission is finished, and further makes the sensor panel output first image data corresponding to the first x-ray radiation emission and second image data corresponding to the second x-ray radiation emission, and
   the preview image producing portion produces the preview image based on the first image data.

8. The x-ray radiation imaging system according to claim 7, wherein the preview image producing portion subjects the first image data to binning processing or thinning processing to produce the preview image.

9. The x-ray radiation imaging system according to claim 7, wherein the x-ray radiation image detecting device further comprises an image addition portion for adding up the first image data and the second image data to produce the x-ray radiation image for diagnosis.

10. The x-ray radiation imaging system according to claim 9, wherein
    the x-ray radiation image detecting device further comprises a first body motion detecting portion for detecting presence or absence of body motion of the object in the first x-ray radiation emission and the second x-ray radiation emission based on a comparison result between the first image data and the second image data, and
    the image addition portion does not operate in the case where the first body motion detecting portion detects body motion of the object.

11. The x-ray radiation imaging system according to claim 10, further comprising a warning section for displaying a warning in the case where body motion of the object is detected by the first body motion detecting portion.

12. The x-ray radiation imaging system according to claim 7, wherein the x-ray radiation image detecting device further comprises a first imaging condition determining section for determining an irradiation time of the second x-ray radiation emission or a tube current-time product as a product of a tube current and an irradiation time, which is to be set in the source controller, as an item of an imaging condition for the second x-ray radiation emission based on the first image data.

13. The x-ray radiation imaging system according to claim 3, wherein the x-ray radiation image detecting device further comprises a plurality of dose detection sensors each for detecting a dose of radiation reaching the imaging area in the first x-ray radiation emission and outputting a dose signal corresponding to the detected dose in order to perform exposure control of the x-ray radiation image for diagnosis.

14. The x-ray radiation imaging system according to claim 13, wherein
the data obtaining portion obtains the data for producing the preview image from the dose detection sensors, and
the preview image producing portion produces the preview image based the dose signal.

15. The x-ray radiation imaging system according to claim 14, wherein the control unit makes the sensor panel continue the accumulation operation during a period of time from when the first x-ray radiation emission is started to when the second x-ray radiation emission is finished, and further makes the sensor panel perform the readout operation after the second x-ray radiation emission is finished, so as to add up electric charges generated in the first x-ray radiation emission and electric charges generated in the second x-ray radiation emission in the pixels.

16. The x-ray radiation imaging system according to claim 13, wherein the x-ray radiation image detecting device further comprises a second imaging condition determining section for determining an irradiation time of the second x-ray radiation emission or a tube current-time product as a product of a tube current and an irradiation time, which is to be set in the source controller, as an item of an imaging condition for the second x-ray radiation emission based on the dose signal.

17. The x-ray radiation imaging system according to claim 16, wherein
the preview image producing portion subjects the x-ray radiation image for diagnosis to binning processing or thinning processing to produce a second preview image, and
the outputting portion outputs the second preview image to the monitor after the second x-ray radiation emission is finished, and then outputs the x-ray radiation image for diagnosis which is not subjected to the binning processing or the thinning processing to the monitor.

18. An operation method of an x-ray radiation imaging system including an x-ray radiation source for emitting x-ray radiation to an object, a source controller for controlling operation of the x-ray radiation source, and an x-ray radiation image detecting device for acquiring an x-ray radiation image of the object, the x-ray radiation image detecting device comprising a sensor panel having an imaging area in which pixels are arranged, each of the pixels accumulating signal charges that correspond to an x-ray radiation dose and are used for generating the x-ray radiation image for diagnosis, the operation method comprising the steps of:
emitting x-ray radiation twice in performing radiography once to acquire one x-ray radiation image for diagnosis of the object by the source controller;
obtaining data for producing a preview image based on the signal charges being used for generating the x-ray radiation image for diagnosis by first x-ray radiation emission by the x-ray radiation image detecting device, the preview image being displayed on a monitor prior to displaying the x-ray radiation image for diagnosis;
producing the preview image based on the obtained data; and
starting output of the produced preview image to the monitor before second x-ray radiation emission is finished.

19. An x-ray radiation image detecting device for use in an x-ray radiation imaging system including an x-ray radiation source for emitting x-ray radiation to an object, a source controller for controlling operation of the x-ray radiation source such that radiation is emitted twice in performing radiography once to acquire one x-ray radiation image for diagnosis of the object, and a monitor for displaying the x-ray radiation image, the x-ray radiation image detecting device detecting the x-ray radiation image for diagnosis based on radiation having passed through the object, the x-ray radiation image detecting device comprising:
a sensor panel having an imaging area in which pixels are arranged, each of the pixels accumulating signal charges that correspond to an x-ray radiation dose and are used for generating the x-ray radiation image for diagnosis;
a data obtaining portion for obtaining data for producing a preview image based on the signal charges being used for generating the x-ray radiation image for diagnosis by first x-ray radiation emission, the preview image being displayed on a monitor prior to displaying the x-ray radiation image for diagnosis;
a preview image producing portion for producing the preview image based on the data obtained by the data obtaining portion; and
an outputting portion for starting output of the preview image produced by the preview image producing portion to the monitor before second x-ray radiation emission is finished.

20. A storage medium for storing an operation program for an x-ray radiation image detecting device which is readable by a computer, the x-ray radiation image detecting device being used in an x-ray radiation imaging system including an x-ray radiation source for emitting x-ray radiation to an object, a source controller for controlling operation of the x-ray radiation source such that radiation is emitted twice in performing radiography once to acquire one x-ray radiation image for diagnosis of the object, a monitor for displaying the x-ray radiation image, and a sensor panel having an imaging area in which pixels are arranged, each of the pixels accumulating signal charges that correspond to an x-ray radiation dose and are used for generating the x-ray radiation image for diagnosis, the x-ray radiation image detecting device detecting the x-ray radiation image for diagnosis based on radiation having passed through the object, the operation program comprising:
a data obtaining step for obtaining data for producing a preview image based on the signal charges being used for generating the x-ray radiation image for diagnosis by first x-ray radiation emission, the preview image being displayed on the monitor prior to displaying the x-ray radiation image for diagnosis;
a preview image producing step for producing the preview image based on the data obtained by the data obtaining step; and
an outputting step for starting output of the preview image produced by the preview image producing step to the monitor before second x-ray radiation emission is finished.

* * * * *